(12) United States Patent
Lee et al.

(10) Patent No.: US 10,184,010 B2
(45) Date of Patent: Jan. 22, 2019

(54) DUAL-TARGETING PROTEIN BINDING SPECIFICALLY TO DLL4 AND VEGF AND USE THEREOF

(71) Applicant: ABLBIO, Seoul (KR)

(72) Inventors: Dong Heon Lee, Daejeon (KR); Kyung Duk Moon, Daejeon (KR); Yu Bin Choi, Daejeon (KR); Kyung Jae Kang, Daejeon (KR); Dong In Kim, Daejeon (KR); Jin Hyung Ahn, Daejeon (KR); Weon Kyoo You, Daejeon (KR); JinWon Jung, Daejeon (KR)

(73) Assignee: ABLBIO, Seoul (KR)

(*) Notice: Subject to any disclaimer, the term of this patent is extended or adjusted under 35 U.S.C. 154(b) by 131 days.

(21) Appl. No.: 14/903,077

(22) PCT Filed: Jul. 8, 2014

(86) PCT No.: PCT/KR2014/006090
§ 371 (c)(1),
(2) Date: Jan. 6, 2016

(87) PCT Pub. No.: WO2015/005632
PCT Pub. Date: Jan. 15, 2015

(65) Prior Publication Data
US 2016/0159929 A1    Jun. 9, 2016

(30) Foreign Application Priority Data

Jul. 9, 2013 (KR) .................. 10-2013-0080523

(51) Int. Cl.
*C07K 16/22* (2006.01)
*C07K 16/28* (2006.01)
*C07K 16/46* (2006.01)
*C12N 15/13* (2006.01)
*C12N 15/63* (2006.01)
*G01N 33/574* (2006.01)
*A61K 39/00* (2006.01)

(52) U.S. Cl.
CPC ............ *C07K 16/468* (2013.01); *C07K 16/22* (2013.01); *C07K 16/28* (2013.01); *G01N 33/57488* (2013.01); *G01N 33/57492* (2013.01); *A61K 2039/505* (2013.01); *C07K 2317/31* (2013.01); *C07K 2317/34* (2013.01); *C07K 2317/622* (2013.01); *C07K 2317/64* (2013.01); *C07K 2317/76* (2013.01); *C07K 2317/92* (2013.01); *G01N 2333/475* (2013.01); *G01N 2333/705* (2013.01)

(58) Field of Classification Search
None
See application file for complete search history.

(56) References Cited

U.S. PATENT DOCUMENTS

2011/0123532 A1    5/2011 Gurney et al.
2011/0189200 A1    8/2011 Skokos

FOREIGN PATENT DOCUMENTS

| CN | 101611055 A | 12/2009 |
|---|---|---|
| CN | 101970004 A | 2/2011 |
| CN | 102076355 A | 5/2011 |
| CN | 102459346 A | 5/2012 |
| CN | 102639566 A | 8/2012 |
| CN | 102753577 A | 10/2012 |
| CN | 104428319 A | 3/2015 |
| KR | 1020090088936 A | 8/2009 |
| KR | 1020110014607 A | 2/2011 |
| KR | 1020110055726 A | 5/2011 |
| WO | 2008076379 A2 | 6/2008 |
| WO | 2009085209 A2 | 7/2009 |
| WO | 2009134776 A2 | 11/2009 |
| WO | 2010040508 A1 | 4/2010 |
| WO | 2010129304 A2 | 11/2010 |
| WO | 2011039370 A1 | 4/2011 |
| WO | 2012061374 A2 | 5/2012 |
| WO | 2013044215 A1 | 3/2013 |
| WO | 2014007513 A1 | 1/2014 |
| WO | 2014071074 A2 | 5/2014 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Li, J., et al., "DLL4-Notch Signaling Mediates Tumor Resistance to Anti-VEGF Therapy in Vivo", "Cancer Research", Jul. 29, 2011, pp. 6073-6083, vol. 71, No. 18.
Yan, M., et al., "Delta-like 4/Notch Signaling and Its Therapeutic Implications", "Clin. Cancer Res.", Dec. 15, 2007, pp. 7243-7246, vol. 13, No. 24.
Li, Q., et al., "Expression and clinical significance of serum DLL4 and VEGF in patients with gastric cancer", "Medical Journal of Qilu", Page(s) Eng Abst, vol. 28, No. 2.
Li, X., et al., "Expression of DLL4 and VEGF in Lung Adenocarcinoma and their Relationship with Angiogenesis in Tumor", "Chinese Journal of Lung Cancer", Feb. 2009, pp. 117-121, vol. 12, No. 2.
Li, X., et al., "Expression of DLL4 and VEGF in Lung Adenocarcinoma and their Relationship with Angiogenesis in Tumor", "Chinese Journal of Lung Cancer", Feb. 2009, Page(s) Eng Abst, vol. 12, No. 2.

* cited by examiner

*Primary Examiner* — Christine J Saoud
*Assistant Examiner* — Jon M Lockard
(74) *Attorney, Agent, or Firm* — Hultquist, PLLC; Steven J. Hultquist

(57) ABSTRACT

The present invention relates to a novel dual-targeting protein comprising: a protein that binds specifically to delta-like ligand 4 (DLL4); and an antibody that binds specifically to vascular endothelial cell growth factor (VEGF).

14 Claims, 13 Drawing Sheets

Specification includes a Sequence Listing.

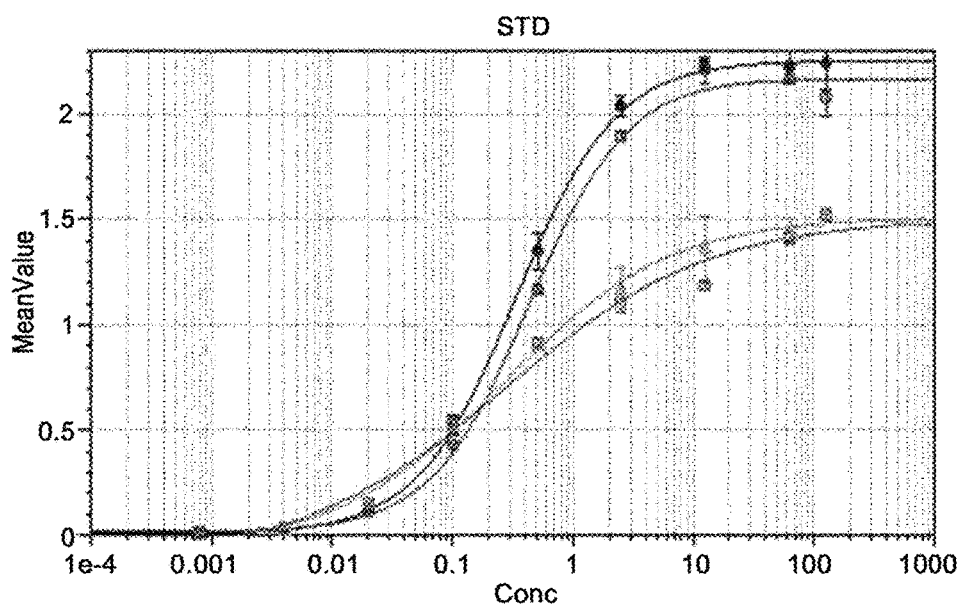

SEQUENCE LISTING

```
<160> NUMBER OF SEQ ID NOS: 23

<210> SEQ ID NO 1
<211> LENGTH: 713
<212> TYPE: PRT
<213> ORGANISM: Artificial
<220> FEATURE:
<223> OTHER INFORMATION: Avastin-anti-Dll4 BsAb VH

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
```

-continued

```
            130                 135                 140
Thr Ala Ala Leu Gly Cys Leu Val Lys Asp Val Phe Pro Glu Pro Val
145                 150                 155                 160
Thr Val Ser Trp Asn Ser Gly Ala Leu Thr Ser Gly Val His Thr Phe
                    165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Tyr Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg His Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys Gly Gly Gly Ser Gly Gly Gly Ser Gly Gly
    450                 455                 460
Gly Gly Ser Gln Ser Val Leu Thr Gln Pro Pro Ser Ala Ser Gly Thr
465                 470                 475                 480
Pro Gly Gln Arg Val Thr Ile Ser Cys Thr Gly Ser Ser Ser Asn Ile
                485                 490                 495
Gly Ser Asn Asp Val Thr Trp Tyr Gln Gln Leu Pro Gly Thr Ala Pro
            500                 505                 510
Lys Leu Leu Ile Tyr Ala Asp Ser Lys Arg Pro Ser Gly Val Pro Asp
        515                 520                 525
Arg Phe Ser Gly Ser Lys Ser Gly Thr Ser Ala Ser Leu Ala Ile Ser
    530                 535                 540
Gly Leu Arg Ser Glu Asp Glu Ala Asp Tyr Tyr Cys Gly Thr Trp Asp
545                 550                 555                 560
```

-continued

Tyr Ser Leu Ser Ala Tyr Val Phe Gly Cys Gly Thr Lys Leu Thr Val
                565                 570                 575
Leu Gly Gly Gly Gly Ser Gly Gly Gly Gly Ser Gly Gly Gly Gly Ser
            580                 585                 590
Gly Gly Gly Gly Ser Glu Val Gln Leu Leu Glu Ser Gly Gly Gly Leu
        595                 600                 605
Val Gln Pro Gly Gly Ser Leu Arg Leu Ser Cys Ala Ala Ser Gly Phe
    610                 615                 620
Thr Phe Ser Asp Tyr Ala Met Ser Trp Val Arg Gln Ala Pro Gly Lys
625                 630                 635                 640
Cys Leu Glu Trp Val Ser Trp Ile Tyr Ser Gly Ser Gly Asn Lys Tyr
                645                 650                 655
Tyr Ala Asp Ser Val Lys Gly Arg Phe Thr Ile Ser Arg Asp Asn Ser
            660                 665                 670
Lys Asn Thr Leu Tyr Leu Gln Met Asn Ser Leu Arg Ala Glu Asp Thr
        675                 680                 685
Ala Val Tyr Tyr Cys Ala Arg Ala Asp Trp Pro Phe Asp Tyr Trp Gly
    690                 695                 700
Gln Gly Thr Leu Val Thr Val Ser Ser
705                 710

<210> SEQ ID NO 2
<211> LENGTH: 10
<212> TYPE: PRT
<213> ORGANISM: Artificial
<220> FEATURE:
<223> OTHER INFORMATION: anti-DLL4 VH CDR1

<400> SEQUENCE: 2

Gly Phe Thr Phe Ser Asp Tyr Ala Met Ser
1               5                   10

<210> SEQ ID NO 3
<211> LENGTH: 17
<212> TYPE: PRT
<213> ORGANISM: Artificial
<220> FEATURE:
<223> OTHER INFORMATION: anti-DLL4 VH CDR2

<400> SEQUENCE: 3

Trp Ile Tyr Ser Gly Ser Gly Asn Lys Tyr Tyr Ala Asp Ser Val Lys
1               5                   10                  15
Gly

<210> SEQ ID NO 4
<211> LENGTH: 7
<212> TYPE: PRT
<213> ORGANISM: Artificial
<220> FEATURE:
<223> OTHER INFORMATION: anti-DLL4 VH CDR3

<400> SEQUENCE: 4

Ala Asp Trp Pro Phe Asp Tyr
1               5

<210> SEQ ID NO 5
<211> LENGTH: 13
<212> TYPE: PRT
<213> ORGANISM: Artificial
<220> FEATURE:
<223> OTHER INFORMATION: anti-DLL4 VL CDR1

```
<400> SEQUENCE: 5

Thr Gly Ser Ser Ser Asn Ile Gly Ser Asn Asp Val Thr
1               5                   10

<210> SEQ ID NO 6
<211> LENGTH: 7
<212> TYPE: PRT
<213> ORGANISM: Artificial
<220> FEATURE:
<223> OTHER INFORMATION: anti-DLL4 VL CDR2

<400> SEQUENCE: 6

Ala Asp Ser Lys Arg Pro Ser
1               5

<210> SEQ ID NO 7
<211> LENGTH: 11
<212> TYPE: PRT
<213> ORGANISM: Artificial
<220> FEATURE:
<223> OTHER INFORMATION: anti-DLL4 VL CDR3

<400> SEQUENCE: 7

Gly Thr Trp Asp Tyr Ser Leu Ser Ala Tyr Val
1               5                   10

<210> SEQ ID NO 8
<211> LENGTH: 116
<212> TYPE: PRT
<213> ORGANISM: Artificial
<220> FEATURE:
<223> OTHER INFORMATION: anti-DLL4 VH

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Cys Leu Glu Trp Val
        35                  40                  45

Ser Trp Ile Tyr Ser Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Trp Pro Phe Asp Tyr Trp Gly Gln Gly Thr Leu Val
            100                 105                 110

Thr Val Ser Ser
        115

<210> SEQ ID NO 9
<211> LENGTH: 110
<212> TYPE: PRT
<213> ORGANISM: Artificial
<220> FEATURE:
<223> OTHER INFORMATION: anti-DLL4 VL

<400> SEQUENCE: 9

Gln Ser Val Leu Thr Gln Pro Pro Ser Ala Ser Gly Thr Pro Gly Gln
1               5                   10                  15
```

```
                        -continued

Arg Val Thr Ile Ser Cys Thr Gly Ser Ser Asn Ile Gly Ser Asn
            20                  25                  30

Asp Val Thr Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Ala Tyr Val Phe Gly Cys Gly Thr Lys Leu Thr Val Leu
            100                 105                 110

<210> SEQ ID NO 10
<211> LENGTH: 10
<212> TYPE: PRT
<213> ORGANISM: Artificial
<220> FEATURE:
<223> OTHER INFORMATION: anti-VEGF VH CDR 1

<400> SEQUENCE: 10

Gly Tyr Thr Phe Thr Asn Tyr Gly Met Asn
1               5                   10

<210> SEQ ID NO 11
<211> LENGTH: 17
<212> TYPE: PRT
<213> ORGANISM: Artificial
<220> FEATURE:
<223> OTHER INFORMATION: anti-VEGF VH CDR 2

<400> SEQUENCE: 11

Trp Ile Asn Thr Tyr Thr Gly Glu Pro Thr Tyr Ala Ala Asp Phe Lys
1               5                   10                  15

Arg

<210> SEQ ID NO 12
<211> LENGTH: 9
<212> TYPE: PRT
<213> ORGANISM: Artificial
<220> FEATURE:
<223> OTHER INFORMATION: anti-VEGF VH CDR 3

<400> SEQUENCE: 12

Tyr Pro His Tyr Tyr Gly Ser Ser His
1               5

<210> SEQ ID NO 13
<211> LENGTH: 11
<212> TYPE: PRT
<213> ORGANISM: Artificial
<220> FEATURE:
<223> OTHER INFORMATION: anti-VEGF VL CDR 1

<400> SEQUENCE: 13

Ser Ala Ser Gln Asp Ile Ser Asn Tyr Leu Asn
1               5                   10

<210> SEQ ID NO 14
<211> LENGTH: 7
<212> TYPE: PRT
<213> ORGANISM: Artificial
<220> FEATURE:
<223> OTHER INFORMATION: anti-VEGF VL CDR2
```

<400> SEQUENCE: 14

Phe Thr Ser Ser Leu His Ser
1               5

<210> SEQ ID NO 15
<211> LENGTH: 9
<212> TYPE: PRT
<213> ORGANISM: Artificial
<220> FEATURE:
<223> OTHER INFORMATION: anti-VEGF VL CDR3

<400> SEQUENCE: 15

Gln Gln Tyr Ser Thr Val Pro Trp Thr
1               5

<210> SEQ ID NO 16
<211> LENGTH: 452
<212> TYPE: PRT
<213> ORGANISM: Artificial
<220> FEATURE:
<223> OTHER INFORMATION: anti-VEGF VH

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Val Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Tyr Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

```
Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg His Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 17
<211> LENGTH: 214
<212> TYPE: PRT
<213> ORGANISM: Artificial
<220> FEATURE:
<223> OTHER INFORMATION: anti-VEGF VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 15
<212> TYPE: PRT
<213> ORGANISM: Artificial
<220> FEATURE:
<223> OTHER INFORMATION: peptide linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 45
<212> TYPE: DNA
<213> ORGANISM: Artificial
<220> FEATURE:
<223> OTHER INFORMATION: peptide linker

<400> SEQUENCE: 19
ggtggaggtg gcagcggtgg tggcggcagt cccggtggcg gctcc            45

<210> SEQ ID NO 20
<211> LENGTH: 214
<212> TYPE: PRT
<213> ORGANISM: Artificial
<220> FEATURE:
<223> OTHER INFORMATION: Avastin-anti-Dll4 BsAb VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                180                 185                 190
Ala Cys Glu Val Thr His Gln Gly Leu Ser Ser Pro Val Thr Lys Ser
        195                 200                 205

Phe Asn Arg Gly Glu Cys
        210

<210> SEQ ID NO 21
<211> LENGTH: 685
<212> TYPE: PRT
<213> ORGANISM: Homo sapiens
<220> FEATURE:
<221> NAME/KEY: BINDING
<222> LOCATION: (58)..(65)
<223> OTHER INFORMATION: hDLL4 epitope1
<220> FEATURE:
<221> NAME/KEY: BINDING
<222> LOCATION: (110)..(115)
<223> OTHER INFORMATION: hDLL4 epitope2

<400> SEQUENCE: 21

Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
```

```
            290                 295                 300
Gln Arg Ser Tyr Thr Cys Thr Cys Arg Pro Gly Tyr Thr Gly Val Asp
305                 310                 315                 320

Cys Glu Leu Glu Leu Ser Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
                355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
                435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
                500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
            530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
            675                 680                 685

<210> SEQ ID NO 22
<211> LENGTH: 8
<212> TYPE: PRT
<213> ORGANISM: Artificial
```

```
<220> FEATURE:
<223> OTHER INFORMATION: hDLL4 epitope1

<400> SEQUENCE: 22

Phe Arg Val Cys Leu Lys His Phe
1               5

<210> SEQ ID NO 23
<211> LENGTH: 6
<212> TYPE: PRT
<213> ORGANISM: Artificial
<220> FEATURE:
<223> OTHER INFORMATION: hDLL4 epitope2

<400> SEQUENCE: 23

Thr Trp Pro Gly Thr Phe
1               5
```

DUAL-TARGETING PROTEIN BINDING SPECIFICALLY TO DLL4 AND VEGF AND USE THEREOF

CROSS-REFERENCE TO RELATED APPLICATIONS

This application is a U.S. national phase under the provisions of 35 U.S.C. § 371 of International Patent Application No. PCT/KR14/06090 filed Jul. 8, 2014, which in turn claims priority of Korean Patent Application No. 10-2013-0080523 filed Jul. 9, 2013. The disclosures of such international patent application and Korean priority patent application are hereby incorporated herein by reference in their respective entireties, for all purposes.

TECHNICAL FIELD

The present invention relates to a novel dual-targeting protein comprising: a protein that binds specifically to delta-like ligand 4 (DLL4) and an antibody that binds specifically to vascular endothelial cell growth factor (VEGF).

BACKGROUND ART

It has been reported that Notch signaling is an evolutionarily highly conserved in vertebrate and invertebrate animals and plays a very pivotal role in determining the fate of cells in the initial stage of development. Notch signaling is known as a major pathway that regulates the differentiation of neural cells, intraocular cells, lymphocytes, muscular cells, hematocytes and the like and is also involved in the development of blood vessels. Mammals have four Notch receptors (Notch 1, 2, 3 and 4), and each of Notch receptors is synthesized as a protein having a size of 300-350 kDa and cleaved at the S1 site by furin-like convertase in the Golgi to form a heterodimer on the cell surface. In addition, four Notch ligands (jagged-1/2 and delta-like ligand (DLL) 1/3/4) were found in mammals.

Activated Notch signaling is known to induce tumorigenesis in various tumor models. When the activated Notch NICD was expressed in rat hematopoietic cells, T-cell leukemia/lymphomas occurred, and activated Notch 1 was found in about 50% of T-ALL (T-cell acute lymphoblastic leukemia). In addition, in the case of breast cancer, Notch 4 receptor was found to be overexpressed in rats (Czech II) introduced with MMTV (mouse mammary tumor virus), and the occurrence of a mammary gland tumor in these rats has been reported. It has been reported that Notch receptors and ligands and Notch signaling targets are activated in various cancers such as cervical cancer, lung cancer, pancreatic cancer, ovarian cancer, breast cancer and prostate cancer. It is known that Notch 1 receptor is associated with worse prognosis on breast cancer patients and associated with the metastasis of prostate cancer.

Delta-like ligand 4 (DLL4) (hereinafter referred to as "DLL4") is one of delta-class ligands that bind to Notch proteins which are overexpressed in vascular endothelial cells. It is known as a major factor that regulates angiogenesis. DLL4 particularly binds to Notch 1 or Notch 4 receptor which is overexpressed in vascular endothelial cells. It is known that DLL4 is highly overexpressed in cancer blood vessels, although it is also expressed in normal blood vessels. Angiogenesis refers to the mechanism by which new blood vessels are formed from the pre-existing blood vessels. Particularly, in tumors, angiogenesis is caused by angiogenic factors such as VEGF (vascular endothelial growth factor) in order to supply oxygen and nutrients to the hypoxia area of cancer tissue. It is known that angiogenesis in tumors plays an important role not only in the growth of the tumor, but also in the metastasis of the tumor. When Notch signaling by DLL4 in tumors is blocked, angiogenesis cannot be easily controlled, and thus the growth of the tumors can be inhibited. In addition, when Notch signaling by DLL4 is inhibited, autoimmune disease can be treated by increasing the number of regulatory T cells (Treg) (US Patent Publication No. 2011-0189200). For these reasons, DLL4 becomes a new target in the treatment of cancers and autoimmune diseases.

Meanwhile, as an anticancer antibody drug for inhibiting angiogenesis, Avastin® (Genentech/Roche) that targets VEGF was approved by the FDA in 2004 and has been largely successful as an anticancer therapeutic agent. However, recent clinical model and preclinical animal model studies have indicated that all solid tumors do not respond to VEGF inhibitors, and have also reported a number of cases in which some tumors treated with VEGF inhibitors in the initial stage show resistance after a certain time. In addition, study results have been reported which indicate that the administration of VEGF inhibitors converts cancer cells into cancer cells that are more aggressive and easily metastasize. Such study reports have propelled research and development of novel anticancer targets that overcome Avastin resistance or that have efficacy superior to that of Avastin. Among such novel anticancer targets, proteins that are involved in the DLL4/Notch signaling pathway are attracting attention. According to the study results reported to date, it is expected that, because the VEGF/VGEFR signaling pathway and the DLL4/Notch signaling pathway influence angiogenesis by different mechanisms, stronger synergistic anticancer effects can be obtained when the two signaling pathways are all inhibited.

DISCLOSURE OF INVENTION

Technical Problem

The present inventors have made extensive efforts to develop a dual-targeting protein which can bind specifically to human-derived DLL4 and VEGF to effectively inhibit the DLL4/Notch and VEGF/VEGFR signaling pathways and can minimize the risk of immunogenicity. As a result, the present inventors have constructed a novel human monoclonal antibody binding specifically to human VEGF, which is a dual-targeting protein wherein a novel ScFv (single-chain variable fragment) that binds specifically to human DLL4 is connected to the C-terminal region of a protein similar to IgG-type Avastin, and have found that such a dual-targeting protein effectively inhibits not only the interaction between VEGF and VEGF receptor, but also the interaction between DLL4 and Notch protein, and thus exhibits excellent anticancer effects, thereby completing the present invention.

Technical Solution

It is an object of the present invention is to provide a dual-targeting protein comprising: a protein binding specifically to DLL4, which recognizes a conformational epitope of DLL4 comprising amino acid residues $58^{th}$ to $65^{th}$ and $110^{th}$ to $115^{th}$ in the amino acid sequence of a DLL4

(delta-like ligand 4) protein represented by SEQ ID NO: 21; and an antibody binding specifically to VEGF (vascular endothelial growth factor).

Another object of the present invention is to provide a polynucleotide encoding the above-described dual-targeting protein, an expression vector comprising the polynucleotide, and a transformant comprising the expression vector.

Still another object of the present invention is to provide a method for producing the dual-targeting protein.

Yet another object of the present invention is to provide a composition comprising the above-described dual-targeting protein.

A further object of the present invention is to provide a pharmaceutical composition for treating cancer, which comprises the above-described dual-targeting protein.

A still further object of the present invention is to provide a composition for diagnosing cancer, which comprises the above-described dual-targeting protein.

A yet further object of the present invention is to provide a method for diagnosing cancer using the above-described dual-targeting protein.

Another further object of the present invention is to provide a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21.

Another still further object of the present invention is to provide a monoclonal antibody binding specifically to DLL4, which recognizes the above-described conformational epitope.

Another yet further object of the present invention is to provide a polynucleotide encoding the monoclonal antibody, an expression vector comprising the polynucleotide, and a transformant comprising the expression vector.

Another yet further object of the present invention is to provide a method for treating cancer, which comprises a step of administering the above-described dual-targeting protein to a subject suspected of having cancer.

Advantageous Effects

The dual-targeting protein according to the present invention can treat cancer by binding to both VEGF and DLL4, and exhibits excellent binding affinity and anticancer effects because it comprises a novel protein that binds specifically to DLL4. Thus, it can be widely used in the fields of cancer treatment and diagnosis.

BRIEF DESCRIPTION OF THE DRAWINGS

FIG. 3 shows the results of an enzyme-linked immunosorbent assay (ELISA) performed to examine the abilities of the dual-targeting protein to bind to DLL4 and VEGF.

BEST MODE FOR CARRYING OUT THE INVENTION

In one aspect, the present invention provides a dual-targeting protein comprising: a protein binding specifically to DLL4, which recognizes a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21; and an antibody binding specifically to VEGF (vascular endothelial growth factor).

As used herein, the term "dual-targeting protein" refers to a protein capable of binding to two different antigens (target proteins). Specifically, the dual-targeting protein does not naturally occur and is preferably produced by a genetic engineering method or any other method.

Figure 1A:
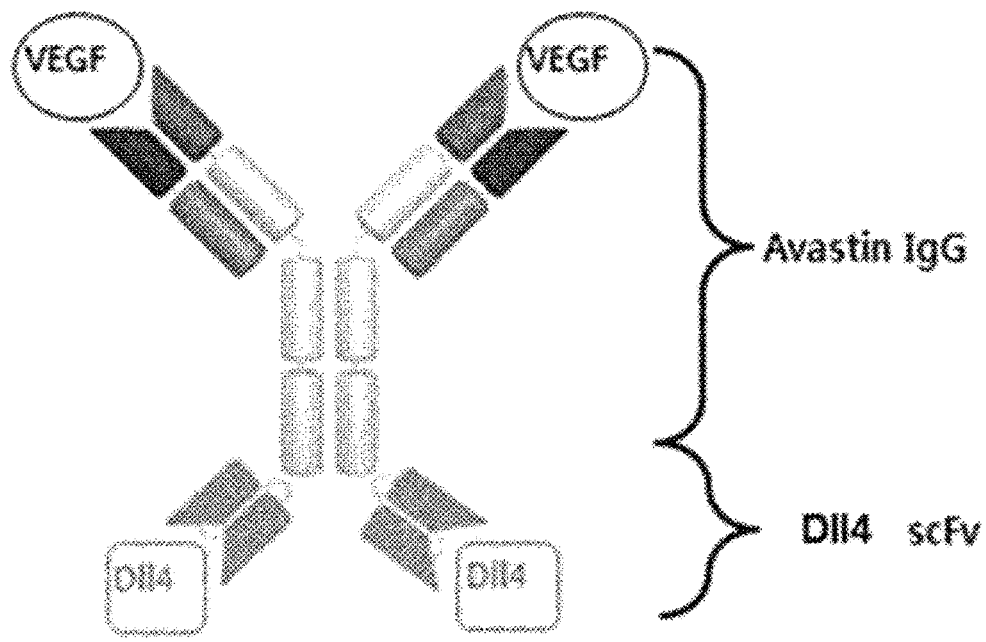
FIGS. 1A and 1B show the structure of a dual-targeting protein capable of binding to both DLL4 and VEGF.

For the purpose of the present invention, the dual-targeting protein can bind to both VEGF that is overexpressed in cancer cells and DLL4 that is expressed in endothelial cells. The dual-targeting protein may be in the form of an antibody. The term "dual-targeting protein", as used herein, may be used interchangeably with the term "dual-targeting antibody", "bispecific antibody" or "bispecific antibody protein". Preferably, the dual-targeting protein of the present invention may target VEGF and DLL4 as antigens. The form of the dual-targeting protein according to the present invention includes a dual-targeting protein form wherein an IgG-type antibody that binds specifically to VEGF and a protein that binds specifically to DLL4 are connected to each other by a linker, but is not specifically limited thereto. The structure of the dual-targeting protein according to the present invention is as schematically shown in FIG. 1A.

Specifically, the dual-targeting protein of the present invention may comprise a heavy-chain amino acid sequence represented by SEQ ID NO: 1 and a light-chain amino acid sequence represented by SEQ ID NO: 20, but is not limited thereto.

As used herein, the term "antibody" refers to a protein molecule which comprises an immunoglobulin molecule immunologically reactive with a particular antigen, and which serves as a receptor that specifically recognizes an antigen. The term may include all polyclonal antibodies, monoclonal antibodies, full-length antibodies, and antibody fragments. In addition, the term may include forms produced by the genetic engineering, such as chimeric antibodies (e.g., humanized murine antibodies) and heterogeneous antibodies (e.g., bispecific antibodies). A full-length antibody has two full-length light chains and two full-length heavy chains, in which each of the light chains is linked to the heavy chain by a disulfide bond. The full-length antibody may comprise IgA, IgD, IgE, IgM and IgG, and subtypes of IgG include IgG1, IgG2, IgG3 and IgG4. In addition, the term antibody may include bivalent molecules, diabodies, triabodies, and tetrabodies. Specifically, the antibodies that bind specifically to VEGF may be IgG type.

In the present invention, the dual-targeting protein may be a form wherein an immunoglobulin G (IgG)-type antibody that binds specifically to VEGF (vascular endothelial growth factor) and a full-length antibody, Fab', F(ab')$_2$, Fab, Fv, rIgG or scFv-type protein that binds specifically to DLL4 (delta-like ligand 4) are connected to each other by a linker.

Typically, an immunoglobulin and scFv have heavy chains and light chains, and each heavy and light chain contains a constant region and a variable region (the regions are also known as domains). Light and heavy chain variable regions contain four framework regions and three hypervariable regions, also called "complementarity-determining regions" (hereinafter referred to as "CDRs"). The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

The dual-targeting protein of the present invention, which comprises a protein that binds specifically to DLL4 and an antibody that binds specifically to VEGF, shows a strong affinity for human-derived DLL4 and VEGF, effectively inhibits the binding of DLL4-expressing cells (e.g., cancer cells or vascular endothelial cells) to Notch 1 or Notch 4 receptor, and also inhibits an angiogenic process in which vascular endothelial cells expressing VEGF receptor are activated by VEGF that is overexpressed in cancer cells. Thus, the dual-targeting protein of the present invention can exhibit a stronger therapeutic effect in the treatment of diseases such as cancer.

The VEGF-specific binding antibody and DLL4-specific binding protein of the dual-targeting protein according to the present invention can maintain their specific binding, and particularly, can simultaneously inhibit two targets (antigens). Thus, the antibody and the protein can be more effective than a protein or antibody that binds to and inhibits a single target, and these can simultaneously inhibit two signals.

As used herein, the term "antibody fragments" refers to fragments having the ability to bind to antigens, and includes antigen-binding forms of antibodies, for example, Fab', F(ab')$_2$, Fab, Fv, rIgG and scFv. In particular, the term "antibody fragments" include scFv (single-chain variable fragment), and particularly, include bivalent molecules or diabodies, triabodies, and tetrabodies.

As used herein, the term "scFv (single-chain variable fragment)" refers to the minimum antibody fragment that contains a complete antigen-recognition and antigen-binding site and comprises antibody VH and VL domains, in which the domains may be present in a single polypeptide chain.

As used herein, the phrase "dual-targeting protein comprising: a protein binding specifically to DLL4, which recognizes a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21; and an antibody binding specifically to VEGF (vascular endothelial growth factor)" may include any dual-targeting protein that can simultaneously inhibit two signaling pathways in which DLL4 and VEGF are involved. The VEGF-specific binding antibody and DLL4-specific binding protein of the dual-targeting protein may be in the form of full-length antibodies and antibody fragments as described above.

As used herein, the phrase "protein binding specifically to DLL4, which recognizes a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21 refers to a protein binding specifically to a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21. The protein means a protein that can exhibit a cancer therapeutic effect by inhibiting the growth of cancer. The protein can bind to the epitope with high affinity, and can function to neutralize DLL4 activity. The protein can block the binding of DLL4 to Notch receptor, and inhibit DLL4-mediated signaling. A protein binding specifically to a conformational epitope of DLL4 comprising amino acid sequences SEQ ID NOs: 21 and 22 may be specifically in the form of full-length antibodies, Fab', F(ab')$_2$, Fab, Fv, rIgG, or scFv (Single-chain variable fragment).

The protein binding specifically to a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21, specifically, the protein that binds specifically to DLL4 may comprise: a heavy-chain variable region comprising heavy-chain CDR1 represented by SEQ ID NO: 2, heavy-chain CDR2 represented by SEQ ID NO: 3, and heavy-chain CDR3 represented by SEQ ID NO: 4; and a light-chain variable region comprising light-chain CDR1 represented by SEQ ID NO: 5, light-chain CDR2 represented by SEQ ID NO: 6, and light-chain CDR3 represented by SEQ ID NO: 7.

More specifically, the heavy chain may comprise a heavy-chain amino acid sequence represented by SEQ ID NO: 8, and the light chain may comprise a light-chain amino acid sequence represented by SEQ ID NO: 9. However, the protein may also be any protein that comprises the above-described CDR sequences and can bind specifically to DLL4 to exhibit a cancer therapeutic effect. The heavy chain and the light chain may be connected to each other by a linker.

In addition, the DLL4-specific binding protein of the dual-targeting protein of the present invention can bind specifically not only to human DLL4, but also to mouse DLL4, and can inhibit the interaction between DLL4 and Notch protein.

In an example of the present invention, the epitope of the DLL4-specific binding antibody of the dual-targeting protein of the present invention, which has an excellent biological activity of inhibiting DLL4 and VEGF, was identified. Specifically, in the present invention, it was found that the antibody binds to the continuous molecular surface of DLL4, which consists of amino acid residues $58^{th}$ to $65^{th}$ and $110^{th}$ to $115^{th}$ in the amino acid sequence of DLL4. Thus, amino acid residues $58^{th}$ to $65^{th}$ (SEQ ID NO: 22) and/or $110^{th}$ to $115^{th}$ (SEQ ID NO: 23) in the amino acid sequence of DLL4 can be the epitope of the DLL4-specific binding antibody according to the present invention. More specifically, a molecular surface region of DLL4, which consists of SEQ ID NOs: 22 and 23, may be a conformational epitope.

As used herein, the term "delta-like ligand 4 (DLL4)" refers to one of delta-class ligands binding to Notch receptors and preferably refers to a protein binding to Notch 1 or Notch 2, but is not limited thereto. DLL4 may be any mammalian DLL4, but is preferably human or mouse DLL4. It is known that DLL4 is overexpressed in various tumor cells including tumor vasculatures and promotes the growth of cancer by increasing the number of abnormal vasculatures in xenograft models.

Thus, the dual-targeting protein of the present invention, which comprises a protein binding specifically to a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21, can be effectively used to treat cancer by inhibiting the function of DLL4. Information about DLL4 can be obtained from known databases, including GenBank of the National Institutes of Health, and may be, for example, information of DLL4 which is GenBank Accession Number NM_019074.3 (Gene ID: 54567 and NCBI Reference Sequence: NM_019074.3). The DLL4 may comprise the amino acid sequence of SEQ ID NO: 21.

As used herein, the term "Notch receptor" refers to a protein that mediates Notch signaling, and may be used interchangeably with Notch. The Notch receptor may be any protein that mediates Notch signaling. Preferably, the Notch receptor may be Notch 1 or Notch 4 receptor, but is not limited thereto.

As used herein, the phrase "inhibiting the interaction between human delta-like ligand 4 (DLL4) and Notch receptor" means that the DLL4-specific binding protein of the present invention binds to DLL4 to inhibit the interaction between DLL4 and Notch receptor. Preferably, the phrase means that the dual-targeting protein specific for the conformational epitope of DLL4, which comprises amino acid residues $58^{th}$ to $65^{th}$ and $110^{th}$ to $115^{th}$ in the amino acid sequence of the DLL4 (delta-like ligand 4) protein represented by SEQ ID NO: 21, binds to DLL4 to inhibit the interaction between DLL4 and Notch 1 or Notch 4 receptor, but is not limited thereto. When the dual-targeting protein of the present invention binds specifically to the conformational epitope of DLL4, which comprises amino acid residues $58^{th}$ to $65^{th}$ and $110^{th}$ to $115^{th}$ in the amino acid sequence of the DLL4 (delta-like ligand 4) protein represented by SEQ ID NO: 21, it prevents Notch receptors from being structurally changed by the binding of DLL4 thereto. Thus, it prevents the hydrolysis of Notch proteins to inhibit Notch signaling. It is known that when DLL4 binds to Notch receptor in tumors, it increases the size of blood vessels and activates the signaling between vascular endothelial cells or Notch signaling between cancer cells and vascular endothelial cells, thereby taking a role in the proliferation and metastasis of tumors.

Thus, when Notch signaling by DLL4 in tumors is inhibited, angiogenesis cannot be easily controlled, and thus the growth of tumors can be inhibited. In addition, when DLL4 is blocked, the loss of lateral inhibition in cells at the end of an angiogenic site appears to cause excessive sprouting, resulting in a decrease in angiogenic reactions having low productivity, and perfusion for supplying oxygen can be reduced to induce hypoxia around tumors, resulting in anti-tumor effects even against tumors showing resistance to anti-VEGF therapy.

Accordingly, the dual-targeting protein of the present invention, which comprises the DLL4-specific binding protein that effectively inhibits the interaction between DLL4 and Notch, can be effectively used for the treatment of cancer.

As used herein, the phrase "antibody that binds specifically to VEGF" or "VEGF-specific binding antibody" includes all antibodies that bind specifically to the antigen VEGF in tumor cells. Specifically, the antibody may be Bevacizumab (Avastin®), a therapeutic antibody that targets VEGF, but is not limited thereto. Such antibodies that bind specifically to VEGF may include full-length antibodies or antibody fragments as described above, and may be IgG antibodies, but are not limited thereto. VEGF is a ligand playing an important role in angiogenesis, and when VEGF is inhibited, no angiogenesis will occur, and thus cancer can be treated. Bevacizumab (Avastin®, Genentech) approved by the US FDA is a therapeutic antibody that can be stably used.

The antibody binding specifically to VEGF, specifically, may comprise: a heavy-chain variable region comprising heavy-chain CDR1 represented by SEQ ID NO: 10, heavy-chain CDR2 represented by SEQ ID NO: 11, and heavy-chain CDR3 represented by SEQ ID NO: 12; and a light-chain variable region comprising light-chain CDR1 represented by SEQ ID NO: 13, light-chain CDR2 represented by SEQ ID NO: 14, and light-chain CDR3 represented by SEQ ID NO: 15. More specifically, the antibody binding specifically to VEGF may comprise a heavy-chain variable region amino acid sequence represented by SEQ ID NO: 16 and a light-chain variable region amino acid sequence represented by SEQ ID NO: 17. However, the antibody may also be any antibody that comprises the above-described CDR sequences and can bind specifically to VEGF to exhibit a cancer therapeutic effect.

The VEGF-specific binding antibody of the dual-targeting protein according to the present invention can bind specifically to VEGF that is overexpressed in tumor cells, and thus can concentrate the dual-targeting protein of the present invention on tumor cells expressing VEGF. Also, it can exhibit anticancer activity by binding to VEGF.

As used herein, the term "vascular endothelial growth factor (VEGF)" refers to a kind of growth factor that enhances the growth activity of vascular endothelial cells and is secreted by various kinds of cells, including macrophages, smooth muscle cells and tumor cells. VEGF plays an important role in fetal angiogenesis, and also functions to induce angiogenesis in order to supply oxygen to tumor tissue in which rapid growth and metabolism occur. Pathways in which VEGF protein and its receptor are involved have been studied as target signaling pathways of anticancer agents in adults.

In addition, the VEGF-binding site of the dual-targeting protein means inhibiting the interaction between human VEGF and VEGF receptor. Specifically, it means that the dual-targeting protein specific for VEGF binds to VEGF to inhibit the interaction between VEGF and VEGFR-2, but is not limited thereto.

For the purpose of the present invention, the VEGF receptor may be any protein that binds to mammalian VEGF. Specifically, it may be a protein that binds to human VEGF.

When the interaction between VEGF and VEGF receptor is inhibited by the VEGF-specific dual-targeting protein of the present invention, VEGF/VEGF signaling by the binding of VEGF to VEGF receptor will be inhibited. It is known that when VEGF and VEGF receptor in tumors bind to each other, VEGF/VEGF receptor signaling in stromal/endothelial cells of cancer tissue is activated to strongly inhibit angiogenesis, unlike the mechanism of the DLL4/Notch signaling pathway, to reduce the number of blood vessels and weaken a vascular function in tumors, thereby inhibiting cancer proliferation and metastasis.

Thus, the dual-targeting protein of the present invention, which is specific for DLL4 and VEGF, shows the ability to inhibit angiogenesis in cancer tissue by a different mechanism, and thus can be used as a therapeutic agent having better anticancer activity.

Specifically, the double-targeting protein may be a form in which the protein that binds specifically to DLL4 and the IgG (immuniglobulin G)-type antibody that binds specifically to VEGF are connected to each other by a linker.

As used herein, the term "linker" refers to any moiety which can connect two different fusion partners (e.g., biological polymers) by use of a hydrogen bond, electrostatic interaction, van der Waals force, a disulfide bond, a salt bridge, hydrophobic interaction, a covalent bond, etc. Specifically, the linker may have at least one cysteine residue which can participate in at least one disulfide bond under physiological conditions or other standard peptide conditions (e.g., conditions for purifying or storing peptides). In addition to connecting the fusion partners, the linker may serve as a spacer and provide a space between the fusion partners or as a hinge to provide flexibility or rigidity for the conjugate. The linker may be a peptidyl linker or a non-peptidyl linker. Direct connection between the fusion partners via a peptide bond or a disulfide bond is within the scope of the role of the linker.

In the present invention, the linker may preferably be a polypeptide which can connect the DLL4-specific binding protein to the VEGF-specific binding antibody, but is not specifically limited thereto. More preferably, the linker may be a peptidyl linker which can connect the C-terminus of the Fc region of the VEGF-specific binding antibody to the DLL4-specific binding protein. More preferably, the linker may be a peptidyl linker comprising an amino acid sequence consisting of three repeats of a GGGGS motif. The GGGGS motif may be repeated 1-10 times. Most preferably, the linker may comprise an amino acid sequence of SEQ ID NO: 18 or an amino acid sequence encoded by a polynucleotide sequence of SEQ ID NO: 19.

```
Linker peptide (SEQ ID NO: 18):
GGGGSGGGGSGGGGS

Linker polynucleotide (SEQ ID NO: 19):
GGTGGAGGTGGCAGCGGTGGTGGCGGCAGTC CCGGTGGCGGCTCC
```

As used herein, the term "non-peptide linker" refers to a biocompatible linker consisting of at least two repeating units which may be connected to each other by any non-peptidyl covalent bond.

Examples of the non-peptide linker that is used in the present invention include polyethylene glycol (PEG) homopolymers, polypropylene glycol homopolymers, ethylene glycol-propylene glycol copolymers, polyoxyethylated polyol, polyvinyl alcohols, polysaccharides, dextran, polyvinyl ethyl ether, biodegradable polymers, lipid polymers, chitins, hyaluronic acid, and combinations thereof. Preferably, the non-peptidyl linker may be a polyethylene glycol homopolymer. Derivatives that have already been known in the art or can be readily prepared on the technical level of the art are within the scope of the present invention. More preferably, the non-peptidyl linker may be a polyethylene glycol homopolymer having a molecular weight of from 1 to 5 kDa. Most preferably, it may be a linker having a molecular weight of 3.4 kDa and containing aldehyde groups at both ends, which can connect VEGF-specific binding antibody to the DLL4-specific binding protein. Particularly, aldehyde functional groups at both ends are effective in minimizing non-specific reactions.

Regions that are connected directly or indirectly via the linker include Fc fragments, Fab', F(ab')$_2$, Fab, Fv and the like, but are not specifically limited thereto. The dual-targeting protein may be: a form in which the whole or part of the DLL4-specific binding protein is connected to the whole or part of VEGF-specific binding antibody; or a form in which the whole or part of the DLL4-specific binding protein is connected to the whole or part of VEGF-specific binding antibody by a peptidyl linker; or a combination thereof, but the dual-targeting protein is not limited thereto.

In addition, The dual-targeting protein may be: a form in which the whole or part of the DLL4-specific binding protein is connected to the whole or part of a heavy chain of VEGF-specific binding antibody by a peptidyl linker; a form in which the whole or part of the DLL4-specific binding protein is connected to the whole or part of a light chain of VEGF-specific binding antibody by a peptidyl linker; or a combination thereof.

Figure 1B:
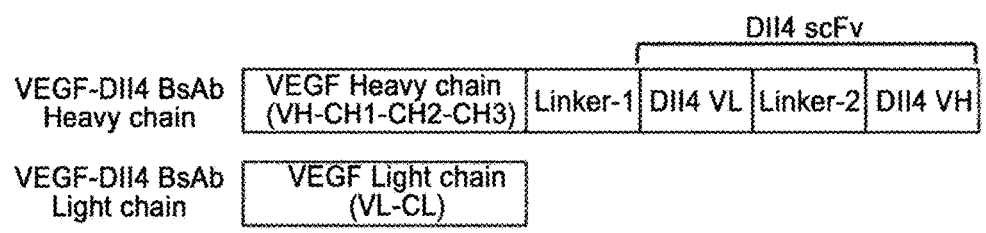
Figure 2A:
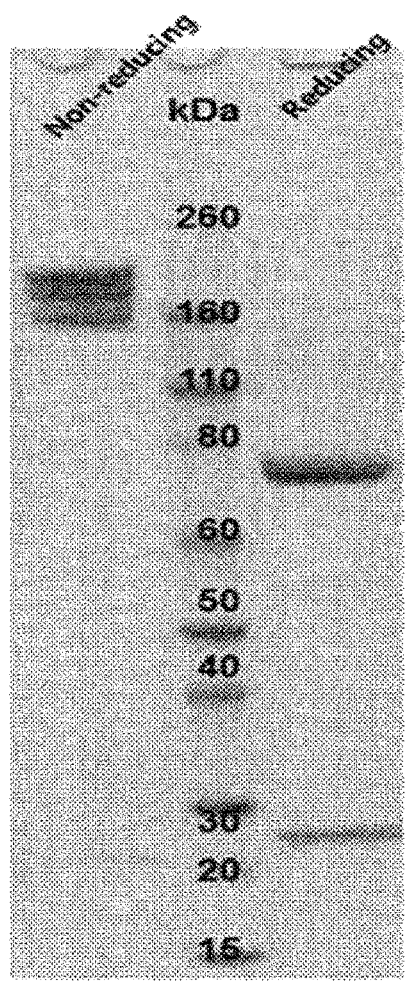
FIG. 2A shows the results obtained by expressing a dual-targeting protein, which can bind to both DLL4 and VEGF, in CHO cells, purifying the expressed protein, and analyzing the purified protein by SDS-PAGE.
Figure 2B:
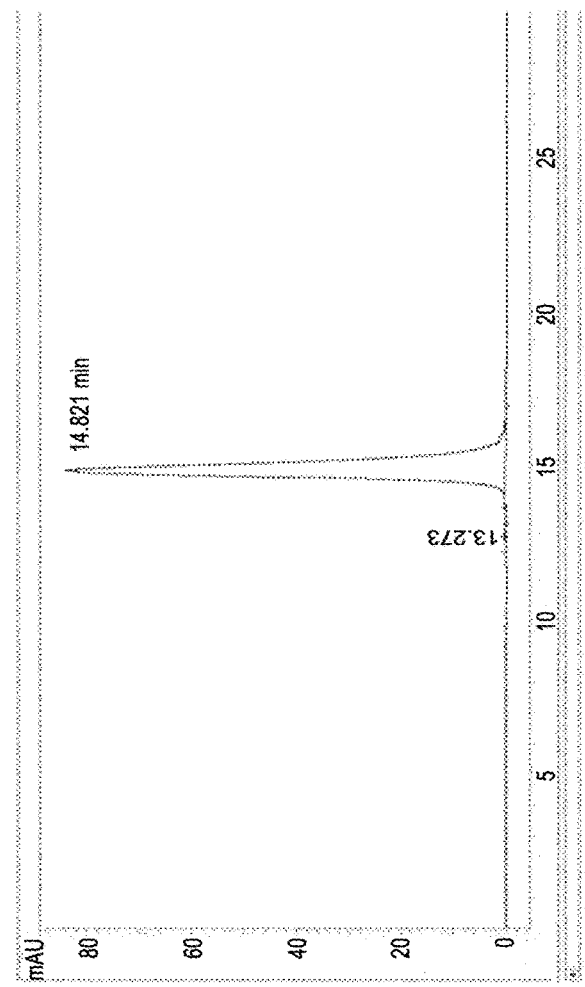
FIG. 2B shows the results obtained by expressing a dual-targeting protein, which can bind to both DLL4 and VEGF, in CHO cells, purifying the expressed protein, and analyzing the purified protein by SEC-HPLC chromatography.
Figure 10:
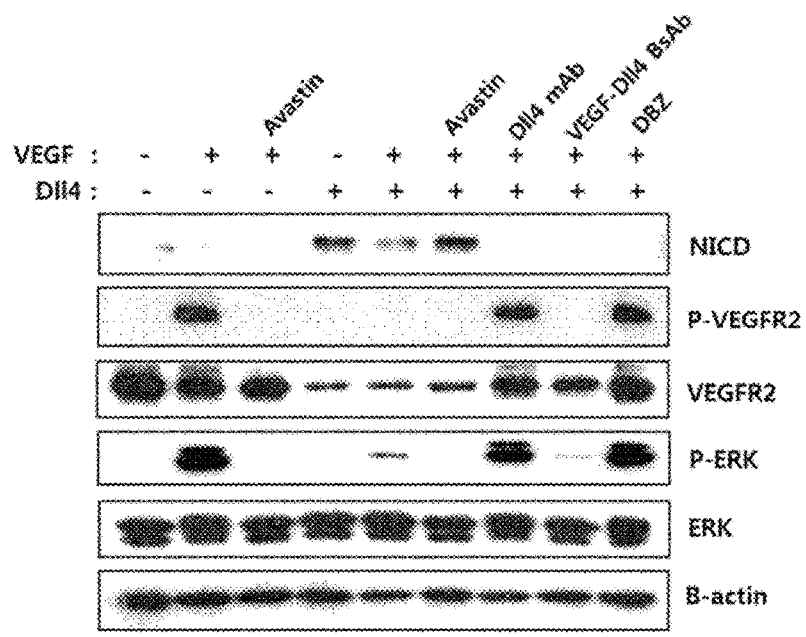
FIG. 10 shows the results of Western blot analysis, which indicate that the dual-targeting protein that binds to DLL4 and VEGF exhibits an activity of inhibiting the DLL4/Notch and VEGF/VEGFR signaling pathways in human umbilical vein endothelial cells (HUVECs).
Figure 11:
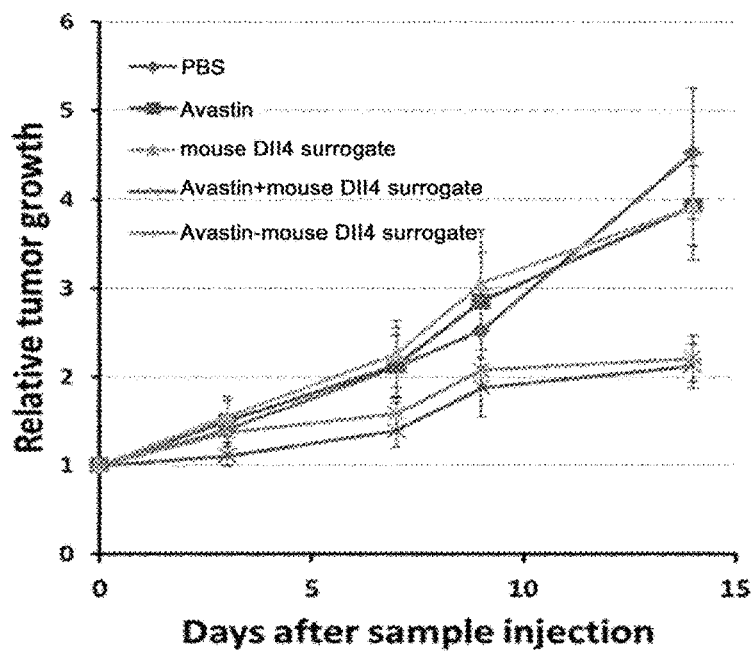
FIG. 11 shows that the dual-targeting protein that binds to DLL4 and VEGF has a stronger anticancer effect than Avastin in an Avastin-resistant human SCH gastric cancer xenograft model constructed in nude mice.
Figure 12:
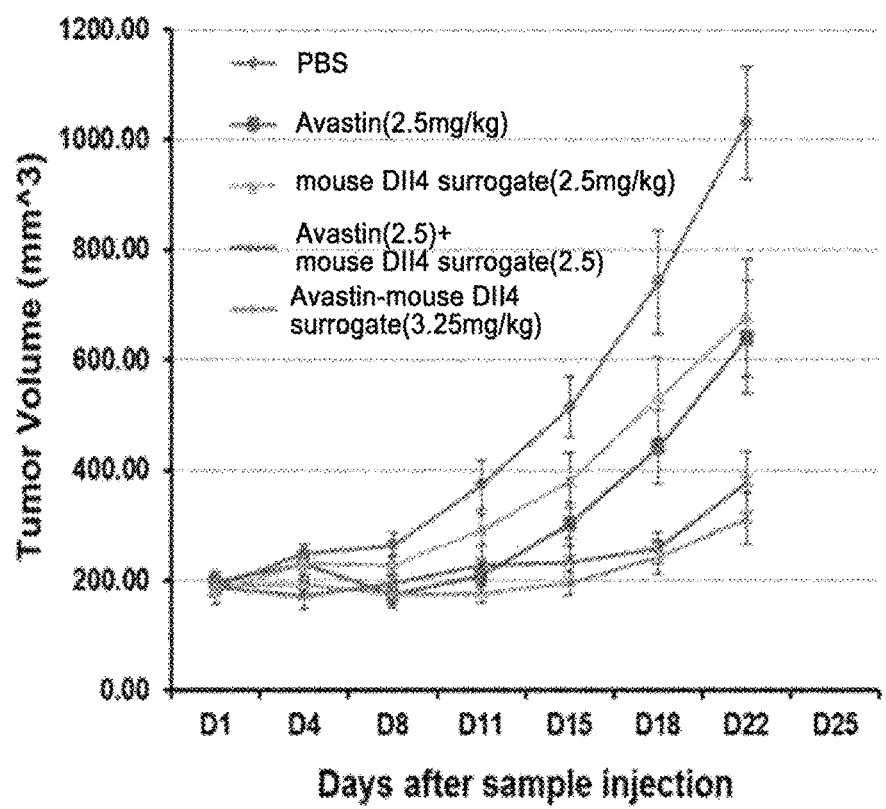
FIG. 12 shows that the dual-targeting protein that binds to DLL4 and VEGF has a stronger anticancer effect than Avastin in an Avastin-resistant human A549 lung cancer xenograft model constructed in nude mice.

In an example of the present invention, the dual-targeting protein Avastin-DLL4 BsAb that binds specifically to DLL4 and VEGF was constructed by connecting the C-terminus of the heavy-chain region of IgG-type Avastin to an scFv-type DLL4-binding protein by a linker to prepare a dual-targeting protein-encoding polynucleotide, inserting the polynucleotide into a vector, introducing the vector into animal cells, and isolating an Avastin-DLL4-binding dual-targeting protein from the cells. The dual-targeting protein molecule has a structure in which an Avastin IgG antibody molecule is connected to a DLL4-binding scFv by a linker (FIG. 1). The Avastin-DLL4-binding dual-targeting protein expressed in animal cells was isolated, and the expression and purity thereof were measured (FIGS. 2A and 2B). In addition, it was found that the Avastin-DLL4-binding dual-targeting protein binds specifically to the targets VEGF and DLL4 (FIG. 3). In addition, it was shown that the binding affinity of the dual-targeting protein for each of the antigens was similar to that of a control antibody. Specifically, the dual-targeting protein showed a KD value of 30 nM for human DLL4 and a KD value of 0.126 nM for human VEGF (Tables 2 and 3). Moreover, it was shown that the signaling pathway caused by each of the binding vascular endothelial cell DLL4 and human Notch 1 receptor and the binding of VEGF to VEGF receptor was effectively inhibited by treatment with the dual-targeting protein (FIG. 10). Such results suggest that the dual-targeting protein of the present invention, which is specific for DLL4 and VEGF, can efficiently block the binding of DLL4 to Notch receptor and the binding of VEGF to VEGF receptor, thereby providing an anticancer effect. The anticancer effect of the dual-targeting protein in Avastin-resistant human SCH gastric cancer and A549 lung cancer xenograft models was found (FIGS. 11 and 12).

In another aspect, the present invention provides a polynucleotide encoding the dual-targeting protein, an expression vector comprising the polynucleotide, and a transformant introduced with the expression vector.

An expression vector comprising a polynucleotide encoding the dual-targeting protein according to the present invention is not specifically limited, but may be a vector capable of replicating and/or expressing the polynucleotide in eukaryotic or prokaryotic cells, including mammalian cells (e.g., human, monkey, rabbit, rat, hamster or mouse cells), plant cells, yeast cells, insect cells and bacterial cells (e.g., *E. coli*). Preferably, it may be a vector, which comprises at least one selective marker and is operably linked to a suitable promoter so that the polynucleotide can be expressed in a host cell. More preferably, the vector may comprise the polynucleotide introduced into a phage, plasmid, cosmid, mini-chromosome, virus or retrovirus vector.

The expression vector comprising the polynucleotide encoding the dual-targeting protein may be either an expression vector comprising each polynucleotide encoding the heavy chain or light chain of the dual-targeting protein or an expression vector comprising all the polynucleotides encoding the heavy chain and light chain of the dual-targeting protein.

Cells into which the expression vector of the present invention is to be introduced to form transformants include bacterial cells such as *E. coli, Streptomyces* and *Salmonella typhimurium*; yeast cells; fungal cells such as *Pichia pastoris*; insect cells such as *Drosophila* or *Spodoptera* Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, BHK (baby hamster kidney cells), HEK (human embryonic kidney cells), PERC.6 (human retinal cells), and the like; and plant cells. In an example of the present invention, CHO-S cells were used as host cells.

As used herein, the term "introduction" refers to the delivery of the vector comprising the polynucleotide encoding the dual-targeting protein into a host cell. This introduction may be performed by various methods known in the art, including calcium phosphate-DNA coprecipitation, DEAE-dextran-mediated transfection, polybrene-mediated transfection, electroporation, microinjection, liposome-mediated transfection, liposome fusion, lipofection and protoplast fusion. Also, transfection means delivering a desired material into a cell by means of infection using viral particles. In addition, the vector may be introduced into a host cell by gene bombardment. In the present invention, introduction may be used interchangeably with transfection.

In still another aspect, the present invention provides a method for producing the dual-targeting protein.

Preferably, the method for producing the dual-targeting protein may be a method for producing a dual-targeting protein comprising a protein that binds specifically to DLL4 and an antibody that binds specifically to VEGF (vascular endothelial growth factor), the method comprising the steps of: (a) culturing the transformant to produce a dual-targeting protein; and (b) recovering the dual-targeting protein produced in step (a).

More preferably, the method for producing the dual-targeting protein may be a method comprising the steps of: (a) preparing a polynucleotide encoding an antibody that binds specifically to VEGF, and a polynucleotide encoding a protein which binds specifically to DLL4 and which comprises: a heavy-chain variable region comprising heavy-chain CDR1 represented by SEQ ID NO: 2, heavy-chain CDR2 represented by SEQ ID NO: 3, and heavy-chain CDR3 represented by SEQ ID NO: 4; and a light-chain variable region comprising light-chain CDR1 represented by SEQ ID NO: 5, light-chain CDR2 represented by SEQ ID NO: 6, and light-chain CDR3 represented by SEQ ID NO: 7; (b) connecting the 3' end of the Fc region-encoding polynucleotide portion of the polynucleotide encoding the VEGF-specific binding antibody, prepared in step (a), to the 5' end of the polynucleotide encoding the DLL4-specific binding protein by a linker, thereby obtaining a polynucleotide encoding the dual-targeting protein; (c) cloning the dual-targeting protein-encoding polynucleotide of step (b) to prepare an expression vector; (d) introducing the expression vector of step (c) into a host cell to obtain a transformant, and culturing the transformant; and (e) recovering the dual-targeting protein from the transformant of step (d).

In addition, the method for producing the dual-targeting protein may be a method comprising the steps of: (a) preparing a polynucleotide encoding an antibody that binds specifically to VEGF, and a polynucleotide encoding a protein which binds specifically to DLL4 and which comprises: a heavy-chain variable region comprising heavy-chain CDR1 represented by SEQ ID NO: 2, heavy-chain CDR2 represented by SEQ ID NO: 3, and heavy-chain CDR3 represented by SEQ ID NO: 4; and a light-chain variable region comprising light-chain CDR1 represented by SEQ ID NO: 5, light-chain CDR2 represented by SEQ ID NO: 6, and light-chain CDR3 represented by SEQ ID NO: 7; (b) cloning the polynucleotide of step (a) to prepare an expression vector; (c) introducing the expression vector of step (b) into a host cell to obtain a transformant, and culturing the transformant; and (d) recovering the VEGF-specific binding antibody and the DLL4-specific binding protein from the transformant of step (c), and connecting the C-terminus of the Fc region of the VEGF-specific binding antibody to the N-terminus of the DLL4-specific binding protein by a linker.

The dual-targeting protein of the present invention can be produced by a known recombination technique or biochemical method, and the antibody may be introduced into a suitable host cell and recovered from the culture medium of the transformant.

Specifically, the dual-targeting protein may be isolated by a known isolation method. For example, the dual-targeting protein may be suitably isolated from the culture medium by a conventional purification procedure such as protein A-Sepharose, hydroxyapatite chromatography, gel electrophoresis, dialysis, or affinity chromatography, but is not limited thereto.

In yet another aspect, the present invention provides a composition comprising the dual-targeting protein.

In a further aspect, the present invention provides a pharmaceutical composition for treating cancer, which comprises the dual-targeting protein.

The dual-targeting protein can bind to both DLL4 and VEGF to inhibit the binding of DLL4 and VEGF to Notch and VEGF receptor, thereby inhibiting the growth of cancer. The DLL4/Notch receptor and the VEGF/VEGF receptor are as described above. When the composition of the present invention, which comprises the dual-targeting protein that binds specifically to DLL4 and VEGF, is administered in vivo, it can inhibit the development, proliferation or metastasis of cancer or prevent the progression of cancer, thereby treating cancer.

As used herein, the term "cancer" includes all the kinds of cancers without limitations, but examples of the cancer may include esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's disease, lymphoma, and multiple myeloid blood cancer. As used herein, the term "treatment" refers to all actions that restore or beneficially change the symptoms of cancer by administering the composition.

In addition, the pharmaceutical composition of the present invention may further comprise a pharmaceutically acceptable carrier.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets.

The pharmaceutical composition of the present invention may be formulated in various manners such as an oral or parenteral formulation. For formulations, commonly used diluents or excipients such as fillers, expanders, binders, wetting agents, disintegrants and surfactants, etc., are used. A pharmaceutical composition comprising the compound according to the present invention is formulated using diluents or excipients, such as fillers, extenders, binders, wetting agents, disintegrants or surfactants, which are commonly used. Solid Formulations for oral administration include tablets, pills, powders, granules, capsules, etc. Such Formulations are prepared by mixing the compound of present invention with at least one excipient, such as starch, calcium carbonate, sucrose, lactose, gelatin, etc. In addition to simple expedients, lubricants such as magnesium stearate, talc, etc. may also be added. Liquid Formulations for oral administration, such as suspensions, internal solutions, emulsions, syrups, etc., may include simple diluents, e.g., water and liquid paraffin, as well as various excipients, e.g., wetting agents s, sweeteners, aromatics, preservatives, etc. Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

The pharmaceutical composition may have any one formulation selected from the group consisting of tablets, pills, powders, granules, capsules, suspensions, internal solutions, emulsions, syrups, sterilized aqueous solutions, non-aqueous solvents, lyophilized agents, and suppositories.

The pharmaceutical composition of the present invention is administered in a pharmaceutically effective amount.

As used herein, the term "pharmaceutically effective amount" refers to an amount sufficient to treat diseases at a reasonable benefit/risk ratio applicable to any medical treatment. The effective dosage level of the composition may be determined depending on the subject's type, the disease severity, the subject's age and sex, the type of the disease, the activity of the drug, sensitivity to the drug, the time of administration, the route of administration, excretion rate, the duration of treatment, factors including drugs used in combination with the composition, and other factors known in the medical field. The pharmaceutical composition of the present invention may be administered individually or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this amount can be easily determined by a person skilled in the art.

Figure 4A:
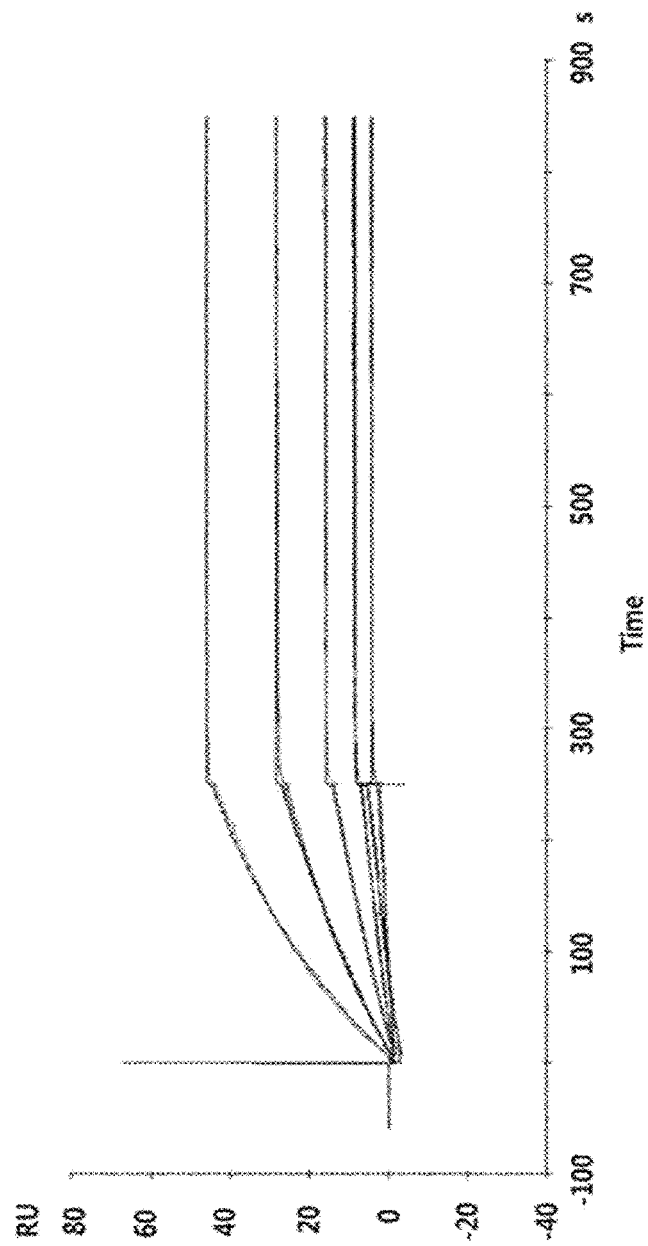
FIG. 4A shows the results of a Biacore assay performed to measure the equilibrium dissociation constant (KD) of the dual-targeting protein for DLL4, an antigen that is targeted by the dual-targeting protein.

In an example of the present invention, it was found that the dual-targeting protein of the present invention could bind to both VEGF and DLL4 (FIGS. 3, 4A and 4B), could neutralize DLL4 (FIG. 5), and exhibited an anticancer effect in Avastin-resistant human SCH gastric cancer and A549 lung cancer xenograft models (FIGS. 11 and 12), indicating that the dual-targeting protein can be used as an active ingredient in compositions for treating cancer.

In still another aspect, the present invention provides a method of treating cancer using a pharmaceutical composition comprising the dual-targeting protein. The method may comprise administering a pharmaceutically effective amount of the pharmaceutical composition.

The dual-targeting protein and the pharmaceutically effective amount are as described above.

The method of treating cancer may comprise administering a pharmaceutical composition comprising the dual-targeting protein together with a pharmaceutically acceptable carrier to a subject having cancer or suspected of having cancer. Herein, the pharmaceutically acceptable carrier and the cancer are as described above. Examples of the subject include mammals, including cattle, pigs, sheep, chickens, dogs, and humans. The subject may be any subject in which cancer is to be treated by administration of the composition of the present invention.

In this case, the composition may be administered in the form of liquid, powder, aerosol, capsule, enteric-coated tablet, or suppository. The composition of the present invention can be administered intraperitoneally, intravenously, intramuscularly, subcutaneously, transdermally, orally, topically, intranasally, intrapulmonarily or intrarectally, but is not limited thereto. However, because the peptide is digested when administered orally, the active ingredient in the composition for oral administration is required to be coated or formulated so as to be protected from degradation in the stomach. In addition, the pharmaceutical composition may be administered by any device by which the active ingredient may be delivered to target cells.

In a still further aspect, the present invention provides a composition for diagnosing cancer, which comprises the dual-targeting protein.

The dual-targeting protein and the cancer are as described above.

As used herein, the term "diagnosing" means detecting the presence or feature of a pathological condition. For the purpose of the present invention, the term "diagnosing" means detecting the onset of cancer.

The composition for diagnosing cancer according to the present invention can be used as follows. The level of VEGF or DLL4 protein on a sample isolated from a subject suspected of having cancer is measured using the dual-targeting protein, and the subject is determined to have cancer, if the measured level of VEGF or DLL4 is higher than that in a normal control sample.

To this end, analysis methods for measuring the amount of the protein include, but are not limited to, immunoblotting (Western blotting), ELISA (Enzyme Linked Immunosorbent Assay), radioimmunoassay (RIA), radioimmunodiffusion, Ouchterlony immunodiffusion, rocket immunoelectrophoresis, immunohistostaining, immunoprecipitation assay, complement fixation assay, FACS, and protein chip assay. The levels of VEGF or DLL4 protein in a normal control sample and a subject suspected of having cancer can be compared with each other through the analysis methods, and thus the onset of cancer of a patient suspected of having cancer can be diagnosed actually.

The composition for diagnosing cancer according to the present invention may further comprise, in addition to the dual-targeting protein, those known in the art which are required to perform the method for measuring the level of the protein.

In a yet further aspect, the present invention provides a method for diagnosing cancer, comprising the steps of: (a) measuring the level of VEGF or DLL4 protein in a sample, isolated from a subject suspected of having cancer, using the dual-targeting protein; and (b) determining that the subject has cancer, if the level of VEGF or DLL4 protein measured in step (a) is higher than that in a normal control sample.

Herein, the dual-targeting protein, the cancer, the subject, the diagnosing, and the method (step) of measuring the level of the protein, are as described above.

As used herein, the term "sample" is meant to include whole blood, serum, blood, plasma, saliva, urine, phlegm, lymph, cerebrospinal fluid, and interstitial fluid, in which there is a difference in the expression level of VEGF or DLL4 in a cancer patient, but is not limited thereto.

In another further, the present invention provides a conformational epitope of DLL4 comprising amino acid residues $58^{th}$ to $65^{th}$ and $110^{th}$ to $115^{th}$ in the amino acid sequence of a DLL4 (delta-like ligand 4) protein represented by SEQ ID NO: 21.

Figure 7:
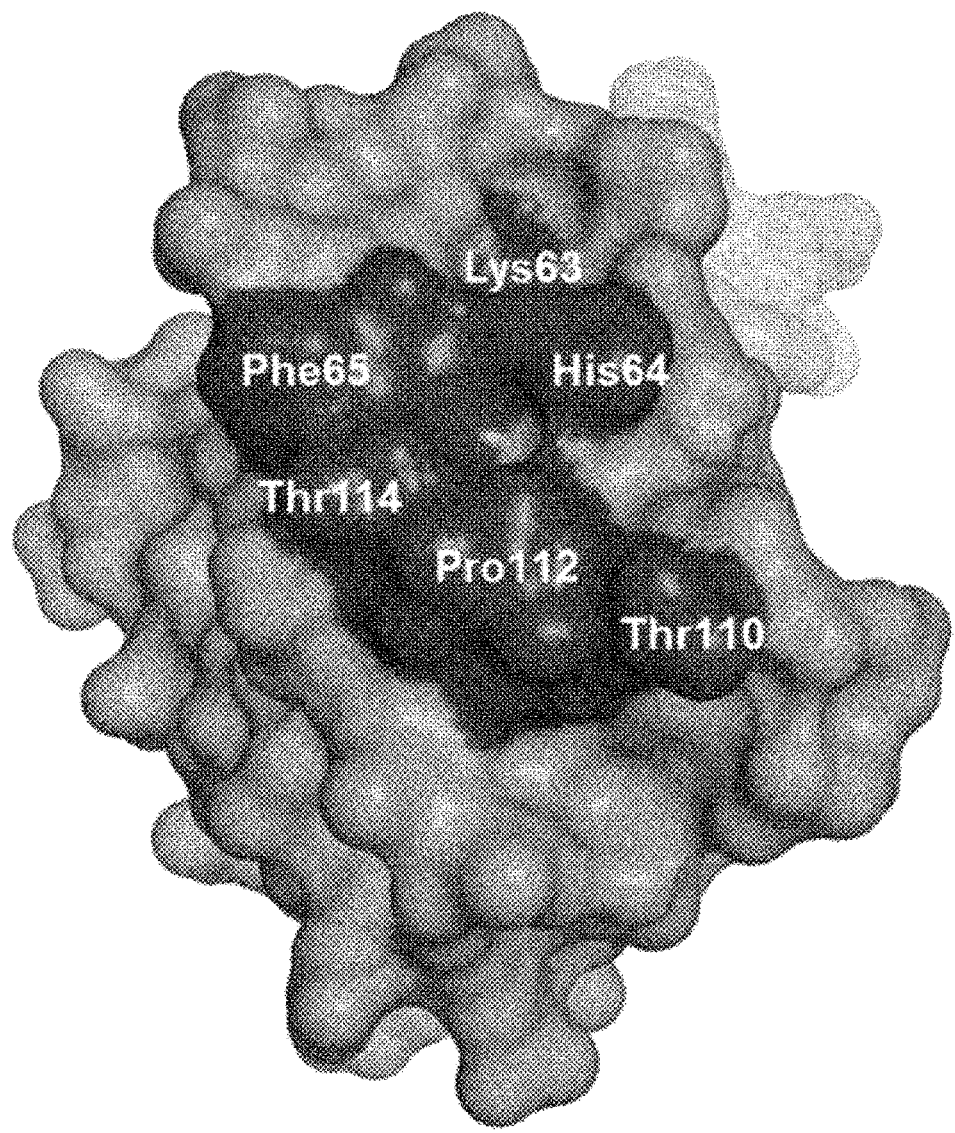
FIG. 7 shows a model in which a fragment consisting of amino acid residues 58-65 [FRVCLKHF]) of the amino acid sequence of DLL4 represented by SEQ ID NO: 21 and a fragment represented by SEQ ID NO: 22 constitute a continuous molecular surface on a human DLL4 C2 domain (amino acid residues 27-174).

In an example of the present invention, amino acid residues in DLL4 of SEQ ID NO: 21, which are cross-linked, were identified by a cross-linking reaction and mass spectrometry. As shown in FIG. 7, it was found that two fragments, an amino acid sequence consisting of amino acid residues $58^{th}$ to $65^{th}$ [FRVCLKHF], and an amino acid sequence consisting of amino acid residues $110^{th}$ to $115^{th}$ (SEQ ID NO: 23), constituted a continuous molecular surface, thereby forming the epitope of DLL4.

In another still further aspect, the present invention provides a monoclonal antibody binding specifically to DLL4, which recognizes the conformational epitope.

Specifically, the monoclonal antibody may comprises: a heavy-chain variable region comprising heavy-chain CDR1 represented by SEQ ID NO: 2, heavy-chain CDR2 represented by SEQ ID NO: 3, and heavy-chain CDR3 represented by SEQ ID NO: 4; and a light-chain variable region comprising light-chain CDR1 represented by SEQ ID NO: 5, light-chain CDR2 represented by SEQ ID NO: 6, and light-chain CDR3 represented by SEQ ID NO: 7. More specifically, the heavy chain may comprise a heavy-chain variable region amino acid sequence represented by SEQ ID NO: 8, and the light chain variable region may comprise a light-chain amino acid sequence represented by SEQ ID NO: 9.

In another yet further aspect, the present invention provides a polynucleotide encoding the monoclonal antibody, an expression vector comprising the polynucleotide, and a transformant introduced with the expression vector.

Herein, the DLL4, the monoclonal antibody, the vector, the transformant, etc., of the present invention are as described above.

In another yet further aspect, the present invention provides a method for treating cancer, which comprises a step of administering the dual-targeting protein to a subject suspected of having cancer.

The subject is a subject in need of the prevention or treatment of cancer, and may be selected from mammals, including humans, cattle, horses, sheep, pigs, goats, camels, antelopes, dogs and cats in need of the treatment of cancer and symptoms similar thereto, but is not limited thereto.

As used herein, the term "administration" means introducing the pharmaceutical composition of the present invention into a patient by any suitable method. The pharmaceutical composition of the present invention may be administered by various oral or parenteral routes, as long as it can reach a desired tissue.

The cancer treatment method of the present invention includes administering the dual-targeting protein or the pharmaceutical composition comprising the dual-targeting protein in a therapeutically effective amount. It is apparent to those skilled in the art that the suitable total daily dose of the composition can be determined by an attending physician or veterinarian within the scope of sound medical judgment. In addition, the composition may be administered one time or several times within the preferred range of its effective amount. In view of the purpose of the present invention, However, the specific therapeutically effective amount for any particular patient will depend upon various factors including the type and extent of response to be achieved, specific compositions according to whether other agents are used therewith or not, the patient's age, body weight, health condition, sex and diet, the time and route of administration, the secretion rate of the composition, the duration of treatment, and other drugs used in combination or coincident with the composition, and other similar factors well-known in the medical field.

EXAMPLES

Hereinafter, the present invention will be described in further detail with reference to examples. It will be obvious to a person having ordinary skill in the art that these examples are for illustrative purposes only and are not to be

Example 1: Preparation of Anti-DLL4/VEGF Dual-Targeting Protein

Example 1-1: Preparation of DLL4 Antigen

As the extracellular domain antigen of human DLL4, human DLL4 protein (Cat: 1506-D4/CF) purchased from R&D System was used. The DLL4 antigen protein comprises amino acid residues 27 to 524 of the amino acid sequence of DLL4 (Accession No. Q9NR61). The C-terminus of the protein has a 10-His tag.

An antigen corresponding to a specific region of the extracellular domain of DLL4 was prepared. This specific region comprises amino acid residues 27 to 251. This region contains a motif called "DSL (delta/Serrate)/lag-2)" domain known to bind to Notch 1 receptor. A mammalian expression vector plasmid comprising a CMV promoter upstream of a polynucleotide encoding a deletion fragment (amino acid residues 27 to 251) of the extracellular domain of DLL4 fused with Fc protein was prepared using a standard recombinant DNA technique. An additional construct encoding the deletion fragment of DLL4, which is a chimera of human DLL4 fused with Fc protein, was prepared using a general recombinant DNA technique. The prepared constructs were transiently transfected into HEK 293E cells to express recombinant fusion proteins comprising amino acid residues 27 to 251 of the amino acid sequence of human DLL4 fused with Fc protein. To recover the antigen protein, conditioning media were collected every 72 hours, and this process was repeated four times. The antigen protein was purified from the conditioning medium by protein A affinity chromatography.

Example 1-2: Preparation of Library Phage $2.7 \times 10^{10}$ human scFv (single-chain variable fragment) library cells having diversity were cultured in a medium (3 l) containing 17 g of 2× YT CM [Tryptone (CONDA, 1612.00), 10 g of yeast extract (CONDA, 1702.00), 5 g of NaCl (Sigma, S7653—5 kg), 34 µg/ml of chloramphenicol (Sigma, C0857)], 2% glucose (Sigma, G5400) and 5 mM $MgCl_2$ (Sigma, M2393) at 37° C. for 2-3 hours ($OD_{600}$=0.5-0.7), after which the cells were infected with helper phage and cultured in 2× YT CMK medium (2× YT CM, 70 µg/ml of kanamycin (Sigma, K1876), 1 mM IPTG (ELPISBIO, IPTG025)) at 30° C. for 16 hours. The cultured cells were centrifuged (4500 rpm, 15 min, 4° C.), and the supernatant was added to and dissolved in 4% PEG (Fluka, 81253) 6000 and 3% NaCl (Sigma, S7653), and then incubated on ice for 1 hour. Next, the solution was centrifuged (8000 rpm, 20 min, 4° C.), and the pellets were added to and dissolved in PBS and then centrifuged (12000 rpm, 10 min, 4° C.). The supernatant comprising library phage was placed in a fresh tube and stored at 4° C.

Example 1-3: Panning by Phage Display

To screen an anti-DLL4 antibody that binds to human DLL4, panning of human DLL4 antigen was performed for 3 rounds.

10 µg/mL of a solution of recombinant human DLL4 (R&D System) was added to an immunotube, and the protein was adsorbed onto the surface of the immunotube overnight at 4° C., and then a solution of 1% bovine serum albumin was added to the immunotube to protect the surface not adsorbed with DLL4. After the immunotube was evacuated, $10^{12}$ CFU of antibody phage library dispersed in 1% bovine serum albumin was added thereto to bind to the antigen. Non-specifically bound phage was washed out with PBS-T (phosphate buffered saline—0.05% Tween 20) solution, and then the remaining antigen-specific phage antibody was recovered using 100 mM triethylamine solution.

The recovered phage was neutralized with 1M tris buffer (pH 7.4) and infected into *E. coli* ER2537 at 37° C. for 1 hour, and the infected *E. coli* cells were plated on carbenicillin-containing LB (Luria-Bertani) agar medium and cultured overnight at 37° C. On the next day, the cultured *E. coli* cells were suspended in 4 mL of SB (superbroth)-carbenicillin medium, and 15% glycerol was added thereto. A portion of the suspension was stored at −80° C., and 50 µl of the remainder was cultured in SB-carbenicillin medium containing 2% glucose at 37° C.

When the absorbance of the culture medium reached 0.6 at 600 nm ($OD_{600}$), the culture medium was removed by centrifugation, and the remaining material was suspended again in 20 mL of SB-carbenicillin medium, and $10^{12}$ PFU of VCSM13 helper phage was added thereto, followed by incubation at 37° C. with slow stirring. On the next day, the culture medium was collected by centrifugation, and precipitated in 4% polyethylene glycol 8000 (PEG8000) and 3% sodium chloride (NaCl) at 4° C. for 30 minutes, followed by centrifugation. The supernatant was removed, and the precipitated phage was suspended in 1 mL of PBS. The above-described panning process was repeated using the suspended phage as a library, thereby amplifying/concentrating antigen-specific clones.

In order to screen an antibody that binds to the Notch 1-binding site of human DLL4 protein, cross-panning of human DLL4 protein and a deletion fragment (amino acid residues 27 to 251) corresponding to a specific region of human DLL4 was performed for rounds. Then, cells were plated and cultured on LB-carbenicillin agar media containing an antibody gene to obtain single colonies, which were then inoculated and incubated in 400 µl of SB-carbenicillin medium, after which the expression of scFv-type protein in the periplasm of *E. coli* was induced by adding IPTG. The *E. coli* cells were suspended in TES solution (Tris, EDTA, sucrose) and allowed to stand at 4° C. for 1 hour. Then, the suspension was centrifuged to extract the periplasm, which was then used to examine the binding between the recombinant human DLL4 antigen and scFv by an ELISA technique.

The bound scFv was detected using a horseradish peroxidase (HRP)-anti-HA antibody and a tetramethylbenzidine (TMB) substrate. The detected antigen-specific antibody clones were sequenced. The results of sequencing of the screened scFv are shown in Table 1 below.

TABLE 1

| Amino Acid Sequences | CDR1 | CDR2 | CDR3 |
| --- | --- | --- | --- |
| $V_H$ EVQLLESGGGLVQPGGSLRL SCAASGFTFSDYAMSWVRQA PGKCLEWVSWIYSGSGNKYY ADSVKGRFTISRDNSKNTLY LQMNSLRAEDTAVYYCARAD WPFDYWGQGTLVTVSS (SEQ ID NO: 8) | GFTFSDYAMS (SEQ ID NO: 2) | WIYSGSGNKYYADSVKG (SEQ ID NO: 3) | ADWPFDY (SEQ ID NO: 4) |
| $V_L$ QSVLTQPPSASGTPGQRVTI SCTGSSSNIGSNDVTWYQQL PGTAPKLLIYADSKRPSGVP DRFSGSKSGTSASLAISGLR SEDEADYYCGTWDYSLSAYV FGCGTKLTVL (SEQ ID NO: 9) | TGSSSNIGSNDVT (SEQ ID NO: 5) | ADSKRPS (SEQ ID NO: 6) | GTWDYSLSAYV (SEQ ID NO: 7) |

The anti-DLL4 antibody having the above sequence was named "MLCK-2".

Example 1-4: Preparation of Dual-Targeting Antibody (Bispecific Antibody) that Targets DLL4 and VEGF The human DLL4-binding scFv-type antibody prepared in Example 1-3 was connected to an Avastin IgG type antibody by use of a linker, thereby preparing a dual-targeting protein expression vector that can also bind to human VEGF (FIG. 1B).

The prepared dual-targeting protein has a heavy-chain amino acid sequence (VEGF-DLL4 BsAb heavy chain) of SEQ ID NO: 1 and a light-chain amino acid sequence of SEQ ID NO: 20. The heavy chain comprises a heavy-chain variable region comprising heavy-chain CDR1 represented by SEQ ID NO: 2, heavy-chain CDR2 represented by SEQ ID NO: 3, and heavy-chain CDR3 represented by SEQ ID NO: 4; and a light-chain variable region comprising light-chain CDR1 represented by SEQ ID NO: 5, light-chain CDR2 represented by SEQ ID NO: 6, and light-chain CDR3 represented by SEQ ID NO: 7.

To produce an antibody in CHO cells using the dual-targeting protein expression vector, the gene of interest was transfected into animal cells using a polymer for increasing intracellular gene delivery efficiency, and the cells were cultured in a 500-ml Erlenmeyer flask (Corning Costar) at a volume of 200 ml per bottle to a total volume of 1 l. 1 l of a mixture of RPMI medium (Invitrogen Corp.) containing ultra-low-IgG fetal bovine serum (Invitrogen Corp.) and CHO cell culture medium was incubated in an incubator (Sanyo) for 4 days, thereby producing a recombinant protein. The cell culture medium was collected and centrifuged to separate the supernatant containing the recombinant protein from the suspended cells, and the supernatant was filtered once through a 0.22-μm vacuum filter (Millipore).

For antibody purification, the Avastin-DLL4 BsAb dual-targeting antibody was first purified from the culture medium using a recombinant protein-A Sepharose column (Hitrap MabSelect Sure, 5 mL, GE healthcare). Specifically, the filtered culture medium was loaded on the recombinant protein-A Sepharose column. The column was washed with a 20-fold volume of 50 mM Tris-Cl (pH7.5), 100 mM NaCl buffer, and washed with a 10-fold volume of 50 mM Na-citrate buffer (pH5.0) to remove impurities. The antibody was eluted with 5 mM Na-citrate 10 mM NaCl buffer (pH3.4) and neutralized with 1M Tris-HCl buffer (pH 8.0).

For second purification, an aggregation of the Avastin-DLL4 BsAb dual-targeting antibody was removed using HiLoad TM 26/60 Superdex 200 Prep grade GL (GE Healthcare). The column was equilibrated with a 2-fold volume of 50 mM Na-phosphate buffer (pH6.0), 20 mM L-Arg, and then the purified Avastin-DLL4 BsAb dual-targeting antibody was allowed to run through the column to separate it according to size.

The fractions purified using the column were analyzed by SDS-PAGE (FIG. 2), and the positive fractions were concentrated by centrifugation using an Amicon Ultra (30,000 MWCO, Millipore) concentrator. Using the same concentrator, buffer replacement with phosphate buffer and concentration were performed. Finally, the antibody was sterile-filtered through a syringe filter having a pore size of 0.22 μm, and the absorbance ($A_{280}$) thereof was measured to determine the antibody concentration.

Example 2: Analysis of Binding Affinities of Dual-Targeting Protein for DLL4 and VEGF by ELISA The binding affinities of the dual-targeting proteins for DLL4 and VEGF were assessed using an ELISA-based solution competition assay. Specifically, a 96-well plate (Nunc-Immuno Plate, NUNC, Rochester, N.Y.) was coated with 50 ng/ml of hVEGF (R&D Systems, cat: 293-VE) and 200 ng/ml of rhDLL4 (R&D Systems, cat: 1506-D4/CF) in an amount of 100 μl per well at 4° C. overnight, and non-specific binding sites were blocked with BSA (bovine serum albumin) for 2 hours. The antibody on the 96-well microtiter plate was diluted 1/5-fold from 128 nM and 64 nM, and 100 μl of each of the dilutions was added to each well of the plate coated with hDLL4 and hVEGF proteins. Then, the plate was incubated for 2 hours, and washed five times with 0.05% tween 20-containing PBS. In order to detect the plate-bound antibody, an HRP-conjugated anti-Fab antibody (Pierce, cat: 31414)) was diluted at a ratio of 1:40,000, transferred to the washed 96-well microtiter plate, and then allowed to react at 37° C. for 1 hour. After the reaction, color development was performed using a colorimetric substrate (3,3',5,5'-tetramethylbenzidine; Sigma-Aldrich). The enzymatic reaction was stopped using 0.5 mol/l of sulfuric acid. The absorbance at 450 nm was measured using SpectraMax 190 (molecular device).

As can be seen in FIG. 3, it was shown that the dual-targeting protein of the present invention did bind specifically to its targets (VEGF and DLL4).

Example 3: Assay for Equilibrium Dissociation Constant (KD) of DLL4/VEGF Dual-Targeting Protein for DLL4 and VEGF The dual-targeting protein (bispecific antibody) purified in Example 1 was named "Avastin-DLL4 BsAb", and the affinities of the purified antibody for the antigens were analyzed as follows. To examine the difference in the binding affinities of the Avastin-DLL4 BsAb dual-targeting antibody for DLL4 and VEGF, a BIACORE assay was performed.

Specifically, Biacore T200 was used in SPR analysis and HBS-EP (10 mM HEPES, pH7.4, 150 mM NaCl, 3 mM EDTA, 0.15% surfactant P20) was used as a running buffer. Surface preparation was done by using a surface preparation target immobilization tool of a wizard program (condition: 25° C., 5 μl/min). Ligands (hVEGF and hDLL4) were diluted in 10 mM sodium acetate buffer (pH 4.5) to final concentrations of 5 μg/ml and 4 μg/ml, respectively, and then immobilized to the surface of CM5 chip by a target immobilization level for each test group. In the immobilization process, two flow cells were included as one set wherein the first and third flow cells were set as a blank, the second flow cell has hVEGF immobilized to the surface thereof, and the fourth flow cell was set as hDLL4 in the present experiment. The first and third flow cells acted as a reference to account for experimental variability due to nonspecific bindings and buffer effects, and in the analysis, subtracted RU values (Fc2–Fc1, and Fc4–Fc3) were used as experimental results. The Avastin-DLL4 BsAb dual-targeting antibody that binds to hVEGF and hDLL4 was diluted in a running buffer to a final molar concentration of 100 nM, serially diluted 1/2 times, and each of the 5 dilutions was analyzed. The sample to be analyzed was prepared to have high purity and high concentration, enough to be diluted more than 100 times at minimum, thereby minimizing buffer effect. All analysis was done by using a wizard program, screening duplicates for each sample and a regeneration step was included in between each analysis step, so that the standard of experiment remains constant.

The experimental results were analyzed by Biaevaluation software version 4.0. At this time, to determine the RU values (Fc2–Fc1 and Fc4–Fc3), the baseline was set to zero, the value measured at a buffer injection part (analyte, 0 nM) was subtracted from a whole sensorgram. Then, the resulting RU value was analyzed by a Bivalent binding model to determine a binding affinity. The factors to be analyzed include $k_a$ (M$^{-1}$s$^{-1}$), $k_d$ (s$^{-1}$), and $K_D$ (M). To be specific, $k_a$ is an association constant demonstrating a binding affinity (recognition), and $k_d$ is a dissociation constant demonstrating stability.

Table 2 below shows the results of analyzing the binding affinity of the dual-targeting protein for hVEGF, and Table 3 below shows the results of analyzing the binding affinity of the dual-targeting protein for hDLL4.

TABLE 2

| Antibody | $K_a$(M$^{-1}$s$^{-1}$) | Kd(s$^{-1}$) | $K_D$ |
|---|---|---|---|
| Avastin-DLL4 BsAb | 1.34E04 | 1.68E-06 | 1.26E-10 |

TABLE 3

| Antibody | $K_a$(M$^{-1}$s$^{-1}$) | Kd(s$^{-1}$) | $K_D$ |
|---|---|---|---|
| Avastin-DLL4 BsAb | 1.94E04 | 5.87E-04 | 3.02E-08 |

Figure 4B:
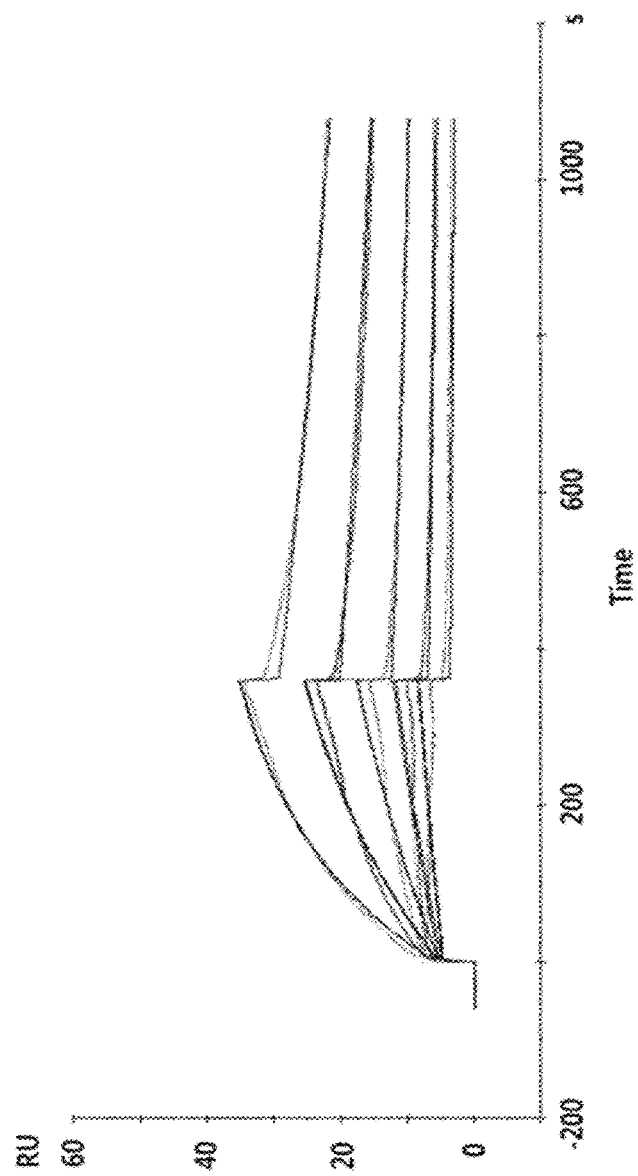
FIG. 4B shows the results of a Biacore assay performed to measure the equilibrium dissociation constant (KD) of the dual-targeting protein for VEGF, an antigen that is targeted by the dual-targeting protein.

As can be seen in Tables 2 and 3 above, equilibrium dissociation constant $K_D$(M) was calculated by dividing $k_d$ with $k_a$ ($k_d/k_a$). The results of analysis of the binding affinity for hVEGF indicated that the $K_D$ value was about 0.126 nM which is similar to the equilibrium dissociation constant of Avastin IgG (FIG. 4A and Table 2), and the results of analysis of the binding affinity for hDLL4 indicated that the $K_D$ value was about 30 nM (FIG. 4B and Table 3). This suggests that the binding affinity of the dual-targeting protein of the present invention for each of the antigens is maintained at a high level without interference.

Example 4: Assay for Neutralization Effect of DLL4/VEGF Dual-Targeting Protein

The neutralization effect of the Avastin-DLL4 BsAb dual-targeting antibody was assessed using an ELISA-based solution competition assay. Specifically, each well of a 96-well microtiter plate (Nunc-Immuno Plate, NUNC, Rochester, N.Y.) was coated with 100 μl of 500 ng/ml of hNotch-1-hFc protein (R&D Systems) (diluted in PBS) at 4° C. overnight, and then treated with BSA for 2 hours to block non-specific binding sites.

Figure 5:
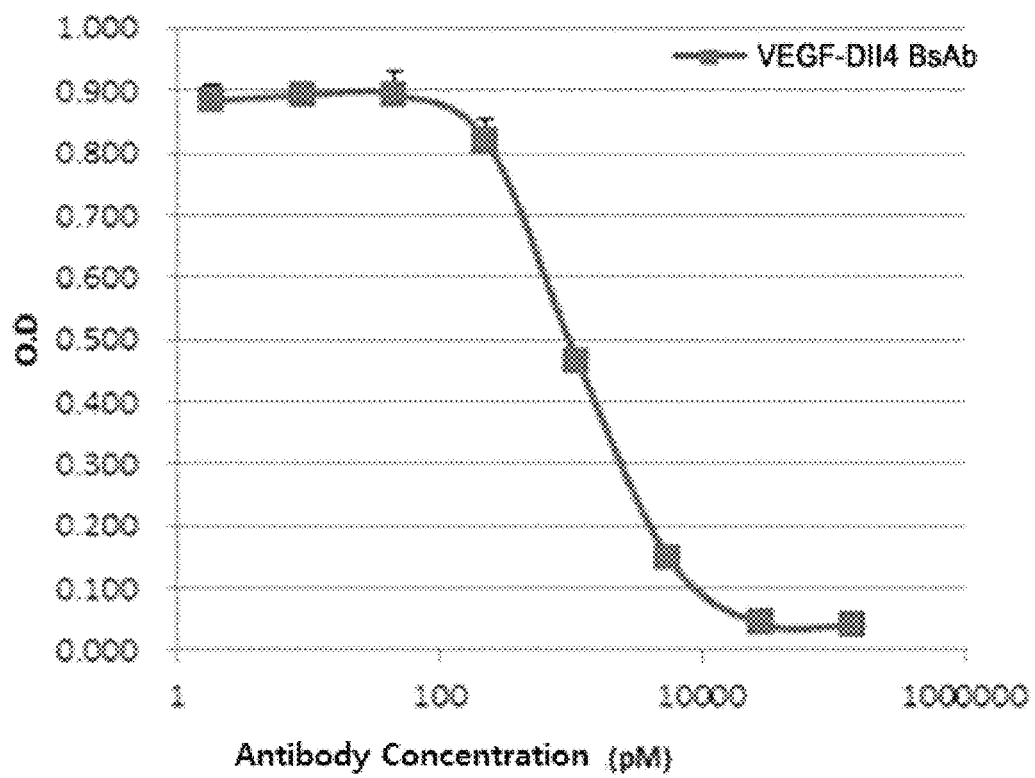
FIG. 5 shows the results of an ELISA performed to measure the abilities of the dual-targeting protein to neutralize DLL4 and VEGF.

The Avastin-DLL4 BsAb dual-targeting antibody (purified protein) on the 96-well microtiter plate was premixed with serial dilutions of antigen protein (human DLL4-His, 600 ng/ml) at an antibody concentration ranging from 0 nM to 140 nM. The antigen/antibody mixture was incubated for 30 minutes, and then transferred to a microtiter plate pre-coated with the DLL4 receptor hNotch-1 protein (50 ng/well) in order to measure free antibody. Then, the plate was incubated for 2 hours and washed five times with 0.05% tween 20-containing PBS. In order to detect the DLL4 antigen bound to the plate, an HRP-conjugated His anti-mouse IgG polyclonal antibody reagent (Roche applied science) was diluted at a ratio of 1:800, and the washed microtiter plate was treated with the diluted antibody reagent, and then allowed to react at 37° C. for 1 hour. Then, color development was performed using a colorimetric substrate (3,3',5,5'-tetramethylbenzidine; Sigma-Aldrich Co.), and the enzymatic reaction was stopped using 0.5 mol/l of sulfuric acid. The absorbance at 450 nm was measured, and the results of the measurement are shown in FIG. 5. The amount of antibody required to achieve a 50% decrease in human DLL4-His bound to plate-coated Notch 1-hFc protein (IC$_{50}$) is shown in Table 4 below.

TABLE 4

| Clone | IC$_{50}$(nM) |
|---|---|
| VEGF-DLL4 BsAb | 1.12 |

As can be seen in Table 4 above, the dual-targeting protein of the present invention showed a low IC$_{50}$ value of 1.12 nM for DLL4, suggesting that it has DLL4 inhibitory activity comparable to that of the anti-DLL4 antibody alone.

Example 5: Epitope Mapping by Cross-Linking Reaction and Mass Spectrometry

In order to identify a conformational epitope, which consists of a plurality of discontinuous sequences but conformationally forms a single molecular surface, a technique of determining the positions of cross-linking reactions by cross-linking reactions and mass spectrometry was used.

Example 5-1: Formation of Cross-Linked Complex

Figure 6:
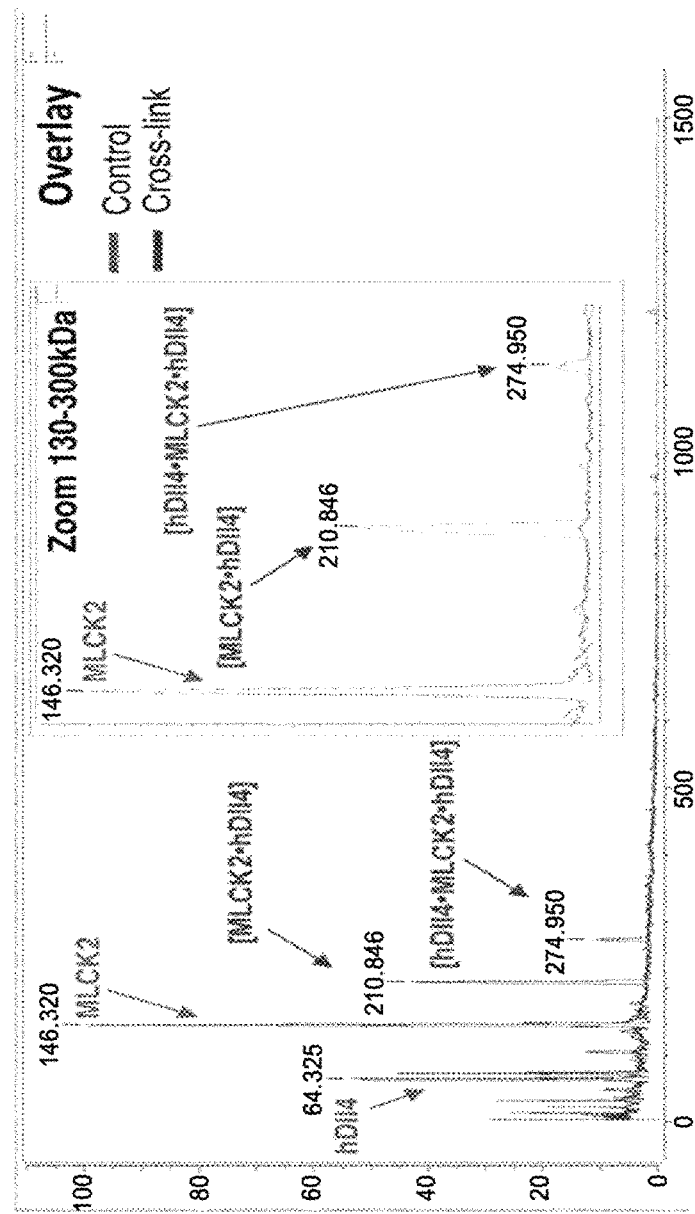
FIG. 6 shows that human DLL4 and MLCK2 antibody form a complex in the presence or absence of a cross-linker.

The antigen protein human delta-like ligand 4 (human DLL4, hDLL4, R&D Systems) and the MLCK2 of Example 1-3 were mixed with each other at a molar ratio of 2:1, and then a K200 cross-linker (CovalX AG) was added thereto at a final concentration of 0.2 mg/ml. The mixture was allowed to react at room temperature for 3 hours to form an antigen-antibody complex, and then the molecular weight of the reaction product was analyzed using an Ultraflex II MALDI ToF spectrometer (Bruker Daltonics). As shown in FIG. 6, it could be seen that when the cross-linker was used, 1:1 and 2:1 complexes between human DLL4 and MLCK2 antibody were formed, unlike a control experiment in which no cross-linker was used. However, it could be seen that when human DLL4 or MLCK2 antibody alone was allowed to react with the cross-linker, any multimer or complex was not detected, suggesting that the formation of the human DLL4/MLCK2 antibody complex results from a specific reaction between DLL4 and MLCK2.

Example 5-2: Formation of Fragments by Protease

In order to identify cross-linked peptide fragments, d0-DSS (disuccinimidyl suberate) and d12-DSS were mixed with each other at a ratio of 1:1 and dissolved in DMF to make 2 mg/ml of a solution. The solution was added to a 2:1 mixture of DLL4 and MLCK2 to a final concentration of 0.2 mg/ml and subjected to a cross-linking reaction at room temperature for 3 hours. The reaction product was modified by reduction and alkylation using DTT (dithiothreitol) and iodoacetamide for effective degradation, and was fragmented using a protease such as trypsin, α-chymotrypsin or ASP-N protease. The produced fragments were analyzed by a Ultimate 3000 nano-liquid chromatography system (Dionex) and an LTQ Orbitrap XL mass spectrometer (Thermo), and the obtained mass spectrometry data were analyzed by Xquest (version 2.0) software and Stavrox (version 2.1) software to detect cross-linked peptide pairs. As a result, as shown in Table 5 below, peptide pairs formed by cross-linking between hDLL4 and MLCK2 could be detected.

Positions on human DLL4, at which a cross-linking reaction occurred, were amino acid residues 59, 63, 64 and 110 of the amino acid sequence of human DLL4. Two fragments, which are an amino acid sequence consisting of amino acid residues $58^{th}$ to $65^{th}$ [FRVCLKHF] (SEQ ID NO: 22) and an amino acid sequence consisting of amino acid residues 110-$115^{th}$ [TWPGTF] (SEQ ID NO: 23), constitute a continuous molecular surface on a human DLL4 C2 domain (27-174) model as shown in FIG. 7. Thus, the two sequences could be determined to be the epitope of human DLL4 for MLCK2 antibody.

TABLE 5

| Sequence | Protein 1 | Protein 2 | Seq. Protein 1 | Seq. Protein 2 | Id-Score | nAA1 | nAA2 | Id on Xquest | Id on Stavrox |
|---|---|---|---|---|---|---|---|---|---|
| ADSVKGRF-TWPGTF-a3-b1 | MLCK2 HC | hDLL4 | 60-67 | 110-115 | 13.62 | 62 | 110 | yes | yes |
| ADSKRPSGVPDRF-FRVCLKHF-a12-b2 | MLCK2 LC | hDLL4 | 50-62 | 58-65 | 11.59 | 62 | 59 | yes | yes |
| ADSKRPSGVPDRF-FRVCLKHF-a3-b7 | MLCK2 LC | hDLL4 | 50-62 | 58-65 | 9.47 | 53 | 64 | yes | yes |
| ADSKRPSGVPDRF-FRVCLKHF-a3-b2 | MLCK2 LC | hDLL4 | 50-62 | 58-65 | 6.33 | 53 | 59 | yes | yes |
| ADSKRPSGVPDRF-FRVCLKHF-a3-b6 | MLCK2 LC | hDLL4 | 50-62 | 58-65 | 6.15 | 53 | 63 | yes | yes |
| ADSKRPSGVPDRF-FRVCLKHF-a4-b2 | MLCK2 LC | hDLL4 | 50-62 | 58-65 | 5.04 | 54 | 59 | yes | yes |

TABLE 5-continued

| Sequence | Protein 1 | Protein 2 | Seq. Protein 1 | Seq. Protein 2 | Id-Score | nAA1 | nAA2 | Id on Xquest | Id on Stavrox |
|---|---|---|---|---|---|---|---|---|---|
| ADSKRPSGVPDRF-FRVCLKHF-a12-b7 | MLCK2 LC | hDLL4 | 50-62 | 58-65 | 3.87 | 62 | 64 | yes | yes |

Example 6: Examination of Epitope Map by Western Blotting

An alanine substitution mutant panel of human DLL4 was prepared as follows, in which each of the amino acid residues at positions 64 (histidine), 65 (phenylalanine) and 69 (valine) in the amino acid sequence of the extracellular protein region of human DLL4 was substituted with alanine. As an expression vector for the alanine substitution mutants, the vector used in the preparation of the antigen corresponding to the specific region of the extracellular domain of DLL4 as described in Example 1-1 was used. Specifically, the vector comprises a gene corresponding to amino acid residues 27 to 251 of the amino acid sequence of the specific region of human DLL4, and this region contains a motif called "DSL (delta/serrate)/lag-2)" which is known to bind to Notch 1 receptor.

Using a standard recombinant DNA technique, a mammalian expression plasmid vector comprising a CMV promoter upstream of a polynucleotide encoding a deletion fragment (amino acid residues 27 to 251) of the extracellular domain of DLL4 fused with Fc protein was prepared. To substitute each of amino acid residues 64, 65 and 69 in the vector with alanine, a recombinant DNA technique (QuikChange Site-Directed Mutagenesis, Agilent) was used, and the mutants were transfected into HEK293E animal cells using Lipofectamine 2000 (Invitrogen) and incubated for 4 days, after which the expression medium was recovered. As a control, a protein encoding a deletion fragment (amino acid residues 27 to 251) of the extracellular domain of wild-type DLL4 was used.

The mutant expression media incubated for 4 days were centrifuged at 1000 rpm at room temperature for 10 minutes to remove the suspended material, and then filtered through a 0.45-μm syringe. For Western blotting analysis, the level of the protein in the mutant expression media were quantified using Octet® system (ForteBio) so that a uniform amount of the mutant would be loaded on SDS gel. Next, 20 μl of each of the mutant expression media was loaded on each of two Novex 4-12% Bis/Tris gels, and subjected to gel electrophoresis using MOPS buffer at 140 V for 50 minutes. As a control, a protein encoding a deletion fragment (amino acid residues 27 to 251) of the extracellular domain of wild-type DLL4 was used. After completion of the electrophoresis, the protein band was transferred to a polyvinylidene difluoride membrane. A total of two processes were performed. In one process, in order to examine whether uniform amounts of the mutant and wild-type proteins were loaded when the deletion fragment (amino acid residues 27 to 251) of the extracellular domain of DLL4 was loaded on SDS gel, an HRP-conjugated anti-human Fc antibody (1:10000) (Pierce Cat: 31413) was bound to the transferred membrane, and then the membrane was washed three times with PBS-T. In the other method, in order to examine the binding affinities of MLCK2 antibody to the mutants, MLCK2 antibody (1 μg/mL) was first bound to the transferred membrane, the membrane was washed three timed with PBS-T, and then an HRP-conjugated anti-human Fab antibody (1:10000) was bound to the membrane, followed by washing three times with PBS-T. Next, Amersham ECL Western blotting detection reagent (GE Healthcare) was applied to the membrane, and signal detection was performed using ImageQuant LAS 4000 (GE Healthcare).

Figure 8:
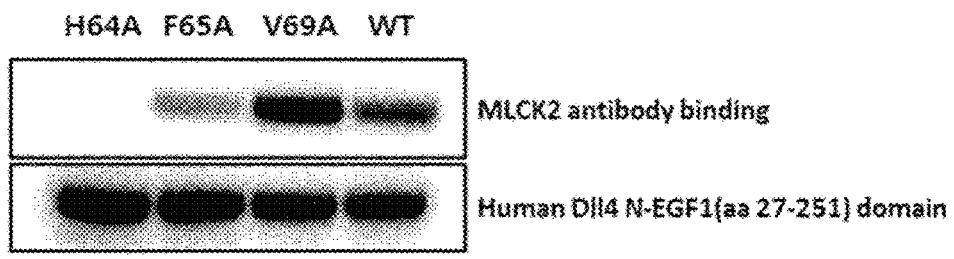
FIG. 8 shows the results of Western blotting performed to examine the binding affinities of mutant proteins encoding a deletion fragment of the extracellular domain of each of wild-type and DLL4.

As shown in FIG. 8, the results of the Western blotting analysis indicated that the mutant proteins encoding the deletion fragment (amino acid residues 27 to 251) of the extracellular domain of wild-type and DLL4 were loaded in a uniform amount. In addition, when the binding affinities of MLCK2 antibody for the mutants were examined, it could be seen that, for the amino acid mutant at position 64, the binding affinity of MLCK2 antibody was lost, and for the amino acid mutant at position 65, the binding affinity of MLCK2 antibody significantly decreased. In addition, it was shown that the amino acid mutant at position 69 did not influence the binding affinity of MLCK2 antibody.

Example 7: Analysis of the Effect of DLL4/VEGF Dual-Targeting Antibody on Proliferation of Human Umbilical Vein Endothelial Cells (HUVECs)

In order to analyze the effect of the dual-targeting antibody, which binds to DLL4 and VEGF, on the proliferation of human umbilical vein endothelial cells (HUVECs), human umbilical vein endothelial cells (HUVECs) purchased from Lonza were used in this experiment.

For culture of HUVECs, T-flask (Nunc) was coated with PBS buffer (Gibco) containing 1% gelatin (Sigma) at a room temperature for 4-6 hours, followed by washing with PBS. EBM-2 containing EGM-2 Single Quot (Lonza) was used as a culture medium, the density of a cell culture was maintained below 80%, and the cells were cultured at 37° C. in a 5% $CO_2$ incubator. The cells before passage 6 were used for this experiment. An HUVEC proliferation assay was done in the following manner. First, to prepare a hDLL4-coated plate, one day before performing the experiment, rhDLL4 (R&D Systems) was diluted in a carbonate buffer to a final concentration of 1 mg/ml in a 96-well plate (BD), and 100 ml of the diluted rhDLL4 was inoculated into each well, and the plate was incubated at 4° C. overnight. In addition, HUVECs were cultured in EBM-2 minimal medium supplemented with 0.1% FBS for 24 hours to minimize the serum effect. On the first day of experiment, each well of the rhDLL4-coated plate was washed twice with PBS, and for each test group, each of hVEGF (50 ng/mL) and antibodies (Avastin: 20 mg/mL; anti-DLL4 antibody alone: 20 mg/mL; Avastin-DLL4 BsAb dual-targeting antibody: 26 mg/mL) was diluted with the EBM-2 minimal medium, and then added to each well in triplicate, followed by incubation at a room temperature for 20 minutes. The HUVECs starved for 24 hours were dissociated into single cells, and diluted to $4\times10^3$ cells/well with EBM-2 minimal medium. The diluted cells were inoculated into the well treated with the antibody and were incubated in a 5% $CO_2$ incubator at 37° C. for 96 hours. After completion of cell proliferation, 10 µl of cell counting kit-8 (CCK-8, Dojino) was added to each well and the plate was incubated in a 5% $CO_2$ incubator at 37° C. for 5 hours. Using SpectraMax 190 (Molecular Devices), the absorption of the sample at 450 nm was measured and the levels of cell proliferation were compared among different test groups.

As shown in all the figures (PBS-treated group) of FIG. 9, when DLL4/Notch signaling is activated, the proliferation of vascular endothelial cells will be inhibited by about 30%, on the contrary to the case in which the proliferation of vascular endothelial cells is activated by VEGF. In the in vivo mechanisms, as described above, it is known that the VEGF antibody inhibits angiogenesis of tumors to thereby inhibit the growth and metastasis of tumors, whereas the DLL4 antibody induces the excessive production of abnormal blood vessels (inactive blood vessels) in tumors to thereby inhibit the growth of tumors. It can be said that the results in FIG. 9 reflect the different angiogenic mechanisms of VEGF and DLL4 in vitro.

Figure 9A:
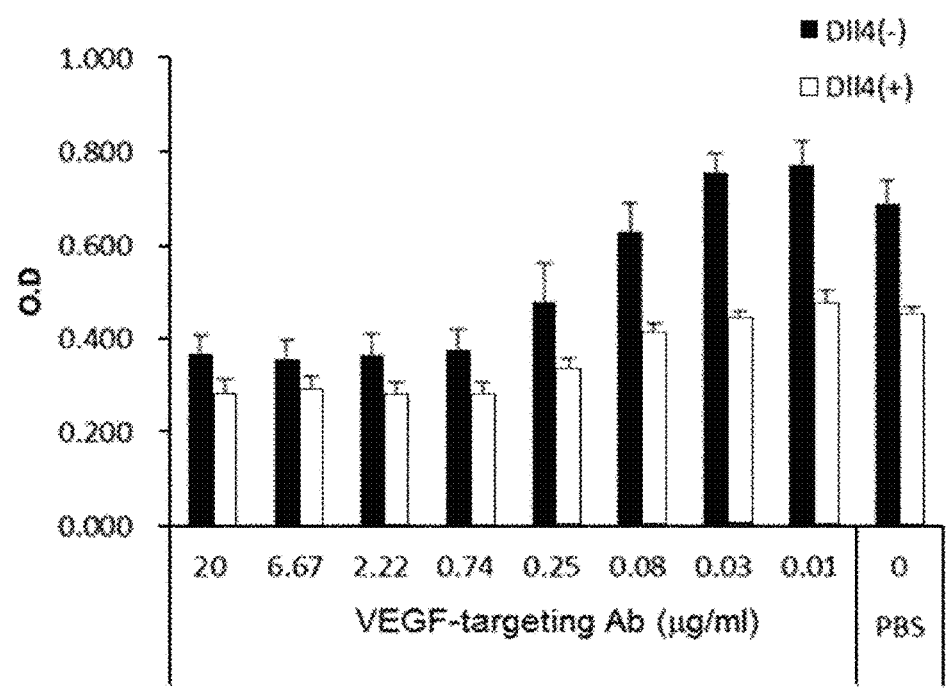
FIG. 9A shows that, when treatment with the VEGF-targeting antibody Avastin was performed, the proliferation of vascular endothelial cells was inhibited in a concentration-dependent manner regardless of the presence or absence of DLL4.
Figure 9B:
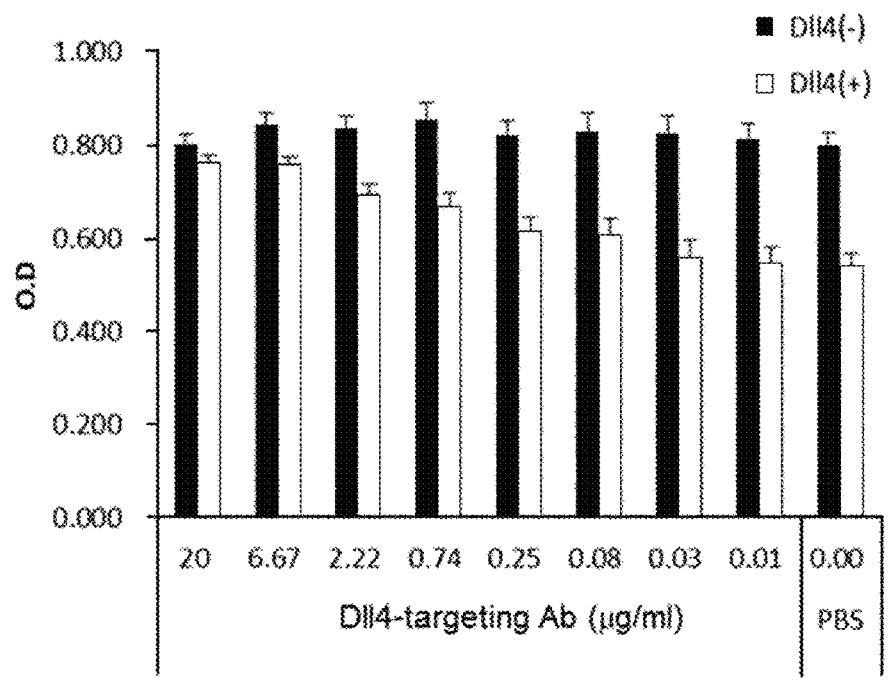
FIG. 9B shows that, when treatment with an antibody against DLL4 alone was performed, the proliferation of vascular endothelial cells appeared only in an experimental group with DLL4 in a manner dependent on the concentration of the anti-DLL4 antibody.
Figure 9C:
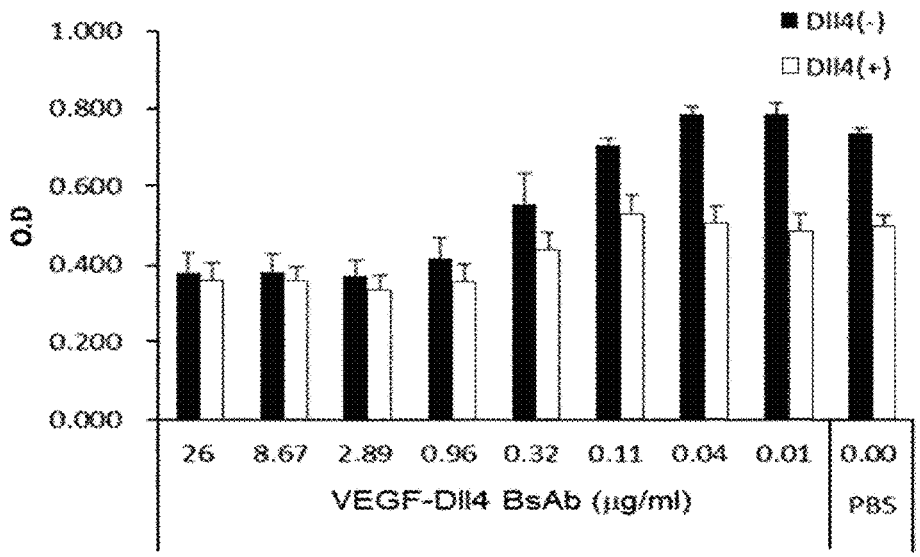
FIG. 9C shows that, when treatment with the dual-targeting protein was performed, an experimental group without DLL4 showed a proliferation inhibitory effect similar to that of treatment with the Avastin antibody (black bars), and an experimental group with DLL4 showed a reduction in the vascular proliferation inhibitory effect compared to Avastin (white bars).

As can be seen in FIG. 9A, when VEGF and its receptor, and the VEGFR signaling pathway, which play an important role in the proliferation of vascular endothelial cells, are treated with the VEGF-targeting antibody (Avastin), the proliferation of vascular endothelial cells was inhibited in a concentration-dependent manner regardless of the presence or absence of DLL4. However, as shown in FIG. 9B showing experimental results obtained by treatment with the DLL4-targeting antibody alone, in the experimental group in which no DLL4 was present, the concentration of the antibody had no significant effect on the proliferation of vascular endothelial cells, and in the experimental group in which DLL4 was present, the proliferation of vascular endothelial cells occurred again in a manner dependent on the concentration of the DLL4-targeting antibody. In the case in which treatment with the dual-targeting protein was performed, in the experimental group in which no DLL4 was present, the dual-targeting protein showed a proliferation inhibitory effect similar to that of treatment with the Avastin antibody (FIG. 9C; black bars), but in the experimental group in which DLL4 was present, the proliferation inhibitory effect of the dual-targeting protein was reduced (FIGS. 9A and 9C; white bars).

From the fact that the group treated with the DLL4-targeting antibody did not show a proliferation inhibitory effect comparable to that of treatment with the VEGF-targeting antibody alone, it can be seen that the dual-targeting antibody of the present invention effectively inhibit both the VEGF and DLL4 signaling pathways.

Example 8: Analysis of Inhibitory Activities of DLL4/VEGF Dual-Targeting Antibody on DLL4/Notch and VEGF/VEGFR Signaling Pathways In order to examine the inhibitory activities of the dual-targeting antibody, which binds to DLL4 and VEGF, on the DLL4/Notch and VEGF/VEGFR signaling pathways, HUVECs were used according to the same method as used in Example 4. Specifically, one day before performing the experiment, a recombinant human DLL4 (rhDLL4, R&D Systems) was diluted with carbonate buffer to a final concentration of 1 mg/ml, and then 1 ml/well of the diluted rhDLL4 was added to a 6-well plate (BD) and incubated at 4° C. overnight. For a control group that was not treated with rhDLL4, 1 ml/well of carbonate buffer was only added to the plate and incubated at 4° C. overnight. On the next day, the DLL4-coated plate was taken from a 4° C. refrigerator and washed once with PBS, and 1 ml of EGM-2 medium was added to each well of the plate. Then, each of antibodies (Avastin: 20 mg/mL; DBZ: 0.08 mM; DLL4-targeting antibody alone: 20 mg/mL; Oncomed DLL4-targeting antibody alone: 20 mg/mL; Avastin-DLL4 BsAb dual-targeting antibody: 26 mg/mL) was added to each well. The final volume of medium in each well was 2 ml and the volume of antibody added was twice the volume of the medium. The plate was incubated for 20 minutes at room temperature. During antibody treatment, the 75T plate containing HUVECs in passages #2 to #5 was taken, and the medium was removed from the plate, and then the cells were dissociated into single cells. Through centrifugation, HUVECs were washed and resuspended in a fresh EGM-2 medium. After counting the cells, the cells were diluted to $5\times10^5$ cells/ml, and 1 ml of the cells were was inoculated into each well and incubated in a 5% $CO_2$ incubator at 37° C. for one day. After culturing HUVECs for one day, the medium was removed from each well, and the cells were washed once with PBS and treated with 2 ml of EBM-2 minimal medium including 0.2% FBS. Also, each well was treated with each of the same concentration of the antibodies (Avastin: 20 mg/mL; DBZ: 0.08 mM; DLL4-targeting antibody alone: 20 mg/mL; Oncomed DLL4-targeting antibody alone: 20 mg/mL; Avastin-DLL4 BsAb dual-targeting antibody: 26 mg/mL) which were treated the day before, and the cells were incubated at 37° C. in a 5% $CO_2$ incubator for one day. Then, each well containing the HUVECs treated with each antibody was treated with 100 ng/ml of hVEGF (R&D Systems) and incubated at 37° C. in a 5% $CO_2$ incubator for 5 minutes. Then the plate was taken out and the medium was removed quickly. The cells were washed once with PBS, and 150 µl of a cell lysis buffer (1% NP-40, 20 mM Tris, 137 mM NaCl, 10% Glycerol, 2 mM EDTA, 1 mM Sodium orthovanabate, 1× Protease & phosphatase inhibitor cocktail) was added to each well, and the plate was shaken to spread the lysis buffer.

Subsequently, the plate was put on ice, and HUVECs were collected from each well using a scraper and put into a 1.5 ml tube and allowed to stand on ice. Every 5 minutes, the 1.5 ml tube containing the cells was taken from ice, vortexed three times, and put on ice again for cell lysis. Then, the sample was centrifuged at 4° C. and 14000 rpm for 10 minutes, and the isolated supernatant was transferred to a fresh tube and weighted. For SDS-PAGE analysis, the supernatant was added to 5×SDS sample buffer and boiled at 100° C. for 10 minutes, followed by SDS-PAGE analysis. At this time, the prepared protein samples were run through 4% to 12% bis-TRIS gel, and separated according to their size, and the separated proteins were Western-blotted with the following antibodies (FIG. 10): NICD (Cell signaling), P-ERK (Cell signaling), ERK (Cell signaling), VEGFR2 (Cell signaling), P-VEGFR2 (Cell signaling), and Actin (Santa Cruz).

As shown in FIG. 10, the dual-targeting antibody of the present invention could inhibit the DLL4/Notch and VEGF/VEGFR signaling pathways to the levels similar to those achieved by the DLL4-targeting antibody alone and the VEGF-targeting antibody alone.

Example 9: Analysis of Anticancer Activity of Dual-Targeting Antibody in Avastin-Resistant Human SCH Gastric Cancer Xenograft Model As reported in literature, human SCH human gastric cancer cells have resistance to Avastin. Thus, an experiment on the effect of the dual-targeting antibody was performed in a nude mouse xenograft model with SCH cells.

Specifically, Avastin-resistant SCH gastric cancer cells were inoculated into female nude mice, and when the tumor size reached an average of 200 mm$^3$, each of antibodies was administered to the mice once a week to confirm the in vivo anticancer activity of the dual-targeting antibody of the present invention (FIG. 11). In this in vivo experiment on the nude mouse xenograft model, the bispecific antibody Avastin-mouse DLL4 surrogate dual-targeting protein that binds to the mouse DLL4 epitope (DSL domain) equal to the human DLL4 epitope (DSL domain) was administered instead of the Avastin-DLL4 dual-targeting antibody that targets human DLL4 in order to demonstrate the excellent anticancer effect of the dual-targeting antibody.

As shown in FIG. 11, the results of the in vivo experiment indicated that the dual-targeting protein of the present invention has a significantly increased anticancer effect against the Avastin-resistant gastric cancer cells.

Example 10: Analysis of Anticancer Activity of Dual-Targeting Antibody in Avastin-Resistant Human A549 Lung Cancer Xenograft Model A549 cells were inoculated into nude mice which were then treated with Avastin (2.5 mg/kg/week) for 3 months, thereby obtaining Avastin-resistant A549 cancer cells whose tumor grows without reducing its size even after treatment with Avastin. The tumor was detached, and then the Avastin-resistant A549 cells were incubated ex vivo in order to analyze the effect of the dual-targeting antibody.

Specifically, Avastin-resistant A549 lung cancer cells were inoculated into female nude mice, and when the tumor size reached an average of 200 mm$^3$, each of antibodies was administered to the mice twice a week to confirm the in vivo anticancer activity of the dual-targeting antibody of the present invention (FIG. 12). In this in vivo experiment using the Avastin-resistant A549 cells, the bispecific antibody Avastin-mouse DLL4 surrogate dual-targeting protein that binds to the mouse DLL4 epitope equal to the human DLL4 epitope was administered instead of the Avastin-DLL4 dual-targeting antibody that targets human DLL4 in order to demonstrate the excellent anticancer effect of the dual-targeting antibody.

As shown in FIG. 12, the results of the in vivo experiment indicated that the dual-targeting protein of the present invention has a significantly increased anticancer effect against the Avastin-resistant lung cancer cells.

From the foregoing, it will be understood by those skilled in the art to which the present invention pertains that the present invention can be carried out in other concrete embodiments without changing the technical spirit or essential feature thereof. In this regard, it should be understood that the aforementioned examples are of illustrative in all aspects but not is limited. The scope of the present invention should be construed to include the meaning and scope of the appended claims, and all the alterations and modified forms which are derived from the equivalent concept thereof, rather than the detailed description.

---

The invention claimed is:

1. A dual-targeting protein comprising: a protein specifically binding to DLL4, which recognizes a conformational epitope of DLL4 comprising amino acid residues 58-65 and 110-115 of SEQ ID NO:21, and an antibody specifically binding to VEGF(Vascular endothelial growth factor), wherein the protein specifically binding to DLL4 comprises:

a heavy chain variable region comprising heavy chain CDR1 having the amino acid sequence of SEQ ID NO:2, heavy chain CDR2 having the amino acid sequence of SEQ ID NO:3, and heavy chain CDR3 having the amino acid sequence of SEQ ID NO:4, and a light chain variable region comprising light chain CDR1 having the amino acid sequence of SEQ ID NO:5, light chain CDR2 having the amino acid sequence of SEQ ID NO:6, and light chain CDR3 having the amino acid sequence of SEQ ID NO:7.

2. The dual-targeting protein of claim 1, wherein the dual-targeting protein is a form in which the protein that binds specifically to DLL4 and an IgG (immunoglobulin G)-type antibody that binds specifically to VEGF are connected to each other by a linker.

3. The dual targeting protein of claim 2, wherein the linker is a peptidyl linker or a non-peptide linker.

4. The dual targeting protein of claim 3, wherein the peptide linker has an amino acid sequence of SEQ ID NO:18.

5. The dual-targeting protein of claim 1, wherein the protein binding specifically to DLL4 comprise the heavy-chain amino acid sequence of SEQ ID NO: 8 and the light-chain amino acid sequence of SEQ ID NO: 9.

6. The dual targeting protein of claim 1, wherein the antibody specifically binding to VEGF comprising:

a heavy chain variable region comprising heavy chain CDR1 having the amino acid sequence of SEQ ID NO:10, heavy chain CDR2 having the amino acid sequence of SEQ ID NO:11, and heavy chain CDR3 having the amino acid sequence of SEQ ID NO:12, and a light chain variable region comprising light chain CDR1 having the amino acid sequence of SEQ ID NO:13, light chain CDR2 having the amino acid sequence of SEQ ID NO:14, and light chain CDR3 having the amino acid sequence of SEQ ID NO:15.

7. The dual targeting protein of claim 1, wherein the antibody specifically binding to VEGF comprising a heavy chain variable region having the amino acid sequence of SEQ ID NO:16 and a light chain variable region having the amino acid sequence of SEQ ID NO:17.

8. The dual-targeting protein of claim 7, wherein the antibody binding specifically to VEGF is Bevacizumab.

9. The dual-targeting protein of claim 1, wherein the dual-targeting protein comprises a heavy chain variable region having the amino acid sequence of SEQ ID NO:1 and a light chain variable region having the amino acid sequence of SEQ ID NO:20.

10. The dual targeting protein of claim 1, wherein the protein binding specifically to DLL4 is in the form of full-length antibodies, Fab', F(ab')2, Fab, Fv, rIgG, or scFv (Single-chain variable fragment).

11. A polynucleotide encoding the dual-targeting protein of claim 1.

12. An expression vector comprising the polynucleotide of claim 11.

13. A transformant introduced with the expression vector of claim 12.

14. A method for producing a dual-targeting protein comprising a protein that binds specifically to DLL4 and an antibody that binds specifically to VEGF (vascular endothelial growth factor), the method comprising the steps of: (a) culturing the transformant according to claim 13 to produce a dual-targeting protein; and (b) recovering the dual-targeting protein produced in step (a).

* * * * *

UNITED STATES PATENT AND TRADEMARK OFFICE
CERTIFICATE OF CORRECTION

PATENT NO. : 10,184,010 B2
APPLICATION NO. : 14/903077
DATED : January 22, 2019
INVENTOR(S) : Dong Heon Lee et al.

It is certified that error appears in the above-identified patent and that said Letters Patent is hereby corrected as shown below:

On the Title Page

The title at (54), and in the Specification at Column 1, Lines 1-3, "DUAL-TARGETING PROTEIN BINDING SPECIFICALLY TO DLL4 AND VEGF AND USE THEREOF" should be -- DUAL-TARGETING PROTEIN COMPRISING A PROTEIN BINDING SPECIFICALLY TO DLL4 AND AN ANTIBODY BINDING SPECIFICALLY TO VEGF AND USE THEREOF --.

Signed and Sealed this
Fifth Day of March, 2019

Andrei Iancu
*Director of the United States Patent and Trademark Office*